US012623083B2

(12) United States Patent
Park et al.

(10) Patent No.: US 12,623,083 B2
(45) Date of Patent: May 12, 2026

(54) SYSTEM AND METHOD FOR INTRA-BODY COMMUNICATION OF SENSED PHYSIOLOGIC DATA

(71) Applicant: TC1 LLC, Wilmington, DE (US)

(72) Inventors: Jin-Woo Park, Duluth, GA (US); Dean P. Andersen, Santa Clara, CA (US); Michael Fonseca, Sylmar, CA (US)

(73) Assignee: TC1 LLC, Wilmington, DE (US)

( * ) Notice: Subject to any disclaimer, the term of this patent is extended or adjusted under 35 U.S.C. 154(b) by 449 days.

(21) Appl. No.: 17/820,654

(22) Filed: Aug. 18, 2022

(65) Prior Publication Data

US 2023/0109023 A1      Apr. 6, 2023

Related U.S. Application Data

(60) Provisional application No. 63/262,115, filed on Oct. 5, 2021.

(51) Int. Cl.
A61N 1/365 (2006.01)
A61N 1/378 (2006.01)

(52) U.S. Cl.
CPC ........... A61N 1/365 (2013.01); A61N 1/3787 (2013.01)

(58) Field of Classification Search
CPC .. A61N 1/365; A61N 1/3787; A61N 1/37211; A61N 1/36139; A61N 1/3702; A61B 5/0215
See application file for complete search history.

(56) References Cited

U.S. PATENT DOCUMENTS

| | | | | |
|---|---|---|---|---|
| 9,168,383 | B2 * | 10/2015 | Jacobson | A61N 1/3756 |
| 9,216,285 | B1 * | 12/2015 | Boling | A61B 5/02444 |
| 9,232,485 | B2 * | 1/2016 | Wu | H04W 4/80 |
| 9,653,926 | B2 * | 5/2017 | Park | A61B 5/0031 |
| 9,894,691 | B1 | 2/2018 | Hellman | |
| 2008/0021333 | A1 * | 1/2008 | Huelskamp | A61B 5/02158 600/486 |
| 2008/0161884 | A1 * | 7/2008 | Chandler | A61N 1/0468 607/148 |
| 2010/0114198 | A1 * | 5/2010 | Donofrio | A61N 1/3962 600/301 |
| 2011/0301479 | A1 * | 12/2011 | Ghanem | A61N 1/3925 600/515 |

(Continued)

*Primary Examiner* — Carl H Layno
*Assistant Examiner* — Dhrasti Snehal Dalal
(74) *Attorney, Agent, or Firm* — Dean D. Small; Carroll, Hoette & Butscher, LLC

(57)      ABSTRACT

A system for collecting real-time on-demand measurements. The system includes an implantable sensor that has a power source, a sensing circuit, a communications circuit, a memory, and one or more processors. The sensing circuit senses a physiologic parameter of interest (PPOI) and generates signals indicative of the PPOI. The communications circuit communicates with at least one of an implantable medical device (IMD) or an external device (ED). The one or more processors execute program instructions stored in the memory to collect real-time on-demand measurements by activating the sensing circuit to generate the signals indicative of the PPOI, converting the signals to physiologic data indicative of the PPOI, storing the physiologic data in the memory, and directing the communications circuit to transmit the physiologic data to the at least one of the IMD or the ED.

25 Claims, 7 Drawing Sheets

(56)　　　　　　References Cited

U.S. PATENT DOCUMENTS

| 2013/0178786 | A1* | 7/2013 | Wariar | ............... | A61N 1/36578 |
| | | | | | 604/20 |
| 2016/0077501 | A1* | 3/2016 | Loverich | ................. | H04W 4/20 |
| | | | | | 700/12 |
| 2016/0242685 | A1* | 8/2016 | DeHennis | ............ | A61B 5/0002 |
| 2019/0015667 | A1* | 1/2019 | Taff | .................... | A61N 1/37205 |
| 2020/0212012 | A1* | 7/2020 | Meyers | ................. | H01L 21/568 |
| 2021/0146144 | A1* | 5/2021 | Jimenez | ............... | A61B 5/0022 |

\* cited by examiner

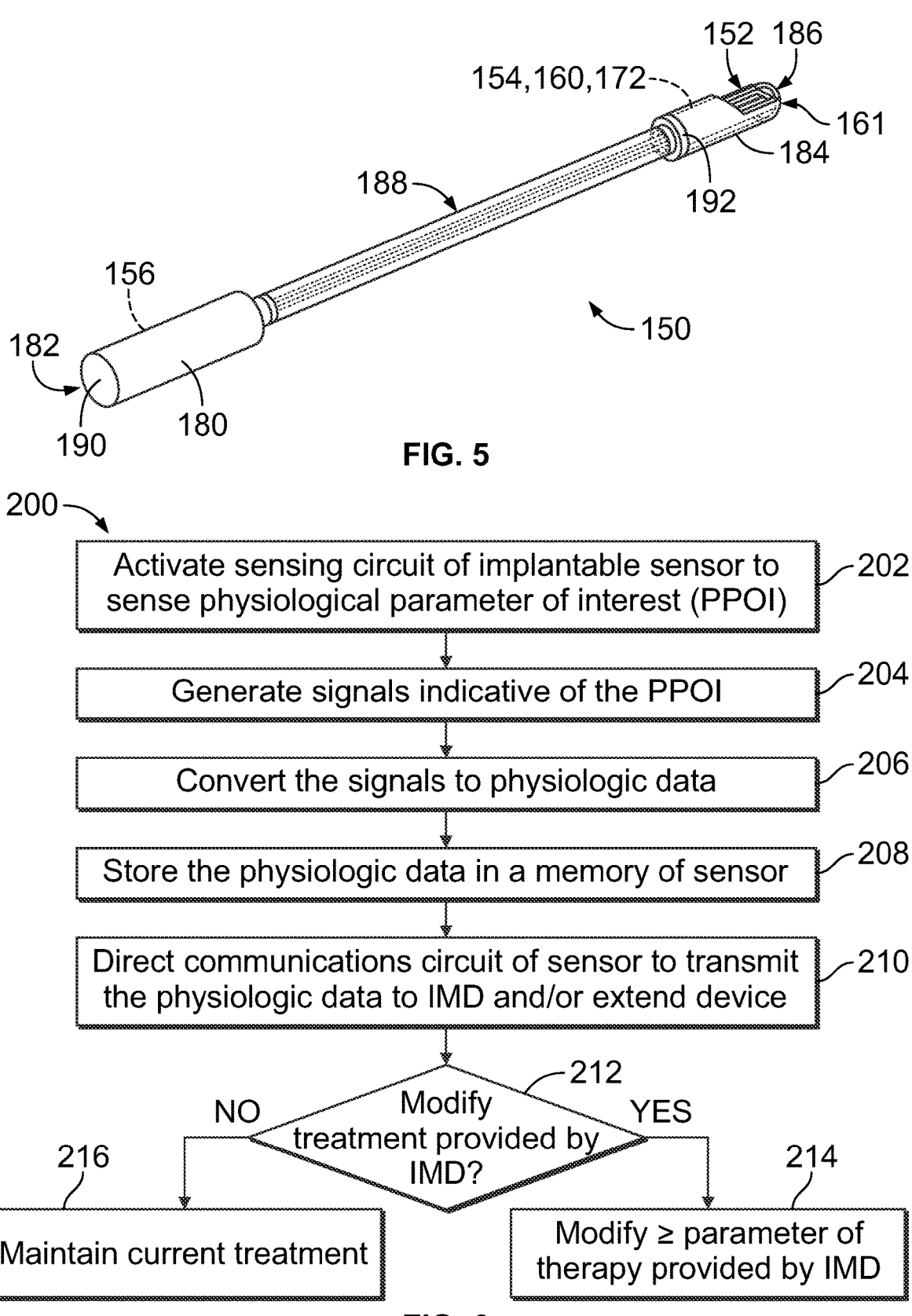

| Activate sensing circuit of implantable sensor to sense physiological parameter of interest (PPOI) | 202 |

| Generate signals indicative of the PPOI | 204 |

| Convert the signals to physiologic data | 206 |

| Store the physiologic data in a memory of sensor | 208 |

| Direct communications circuit of sensor to transmit the physiologic data to IMD and/or extend device | 210 |

212

Modify treatment provided by IMD?

NO

YES

216

214

| Maintain current treatment |

| Modify ≥ parameter of therapy provided by IMD |

FIG. 6

SYSTEM AND METHOD FOR INTRA-BODY COMMUNICATION OF SENSED PHYSIOLOGIC DATA

CROSS-REFERENCE TO RELATED APPLICATIONS

This application claims priority to U.S. Provisional Patent Application No. 63/262,115, filed Oct. 5, 2021. The subject matter of the provisional application is expressly incorporated herein by reference in its entirety.

BACKGROUND

Embodiments of the present disclosure generally relate to methods and devices for communications between implanted sensors, other implanted medical devices within a patient, and external devices outside a patient.

Passive implantable medical sensors are currently available to monitor certain physiologic conditions, such as blood pressure. One example is a pulmonary arterial (PA) pressure sensor. However, passive implantable medical sensors require active patient participation in order to collect the physiologically relevant data and to make the data available to a clinician. For example, PA pressure sensors utilize an external device, outside of the patient body, for supplying energy to the sensors to power the generation and communication of the physiological data. Consequently, the system requires initial patient training and periodic reminders for the patient to utilize the external device for data collection and communication. The physiologic data is analyzed to improve the patient outcome, such as by modifying a treatment of the patient based on the physiologic data generated by the sensor.

The current mechanism, which depends on external devices to power and communicate with the implantable sensor, requires large and highly specialized circuitry within the external device. The circuitry is not available nor easy to integrate in a typical implantable device, such as a pacemaker or cardiac resynchronization therapy (CRT) device. Because user interaction may be required to utilize the external device to activate the passive sensor, the sensor operation may be dependent on patient cooperation and attentiveness. In effect, a sensor may only collect data when it is convenient for the patient, so there may be significant delays between a time at which a physiologic condition of the patient changes and a time in which physiologic data generated by the passive implantable medical sensor indicating that change is communicated for analysis and updating the treatment of the patient based on the change. The physiologically relevant data, that is collected by passive sensor, may not be readily available to other implanted devices such as pacemakers and CRT devices, so the real-time treatment parameter update is not possible.

Furthermore, the size of the passive implantable medical sensors may be limited due to target implant locations within the patient, such as within blood vessels. Due to the size constraint, even if the sensors have an onboard battery, the battery may not be large enough to store sufficient charge to power the physiological data generation and conventional communication operations for an extended period of time.

A need remains for a system and method of communicating sensed physiologic data from an implantable medical sensor for real-time analysis and modification of patient treatment to improve patient outcome, without relying on active patient cooperation or an external energy source to power the sensor at the time of data collection and transmission.

SUMMARY

In accordance with an embodiment, methods, devices and systems are provided that enable implantable sensors such as PA pressure sensors to transmit measured data directly to other implantable medical devices to be analyzed for real-time therapy optimization and disease state diagnosis. The other implantable medical devices may include cardiac resynchronization therapy (CRT) devices, blood glucose monitors, implantable cardiac monitoring devices (ICM), implantable cardioverter defibrillators (ICD), and the like.

In accordance with embodiments herein, an implantable sensor measures a physiologic parameter and generates physiologic data indicative of a value of the physiologic parameter. The sensor transmits the measured physiologic data to a second device, implanted or external, through intra-body communication. The communication mechanism may be radio-frequency (RF), direct wired connection, or wireless conductive communication. The physiologic data is analyzed by the second device, such as an implanted CRT device, a bedside monitoring device, a remote server, or the like, to enhance the therapy delivered to the patient based on the physiologic data. Additionally or alternatively, the physiologic data can be sent from the sensor to a second implantable medical device (IMD) within the patient, such as a CRT device, which transmits the physiologic data externally to an external device outside of the patient. The external device may be a web-enabled device such as a bedside monitor, a hand-held smartphone, a wearable device, or the like, which can store the data in a database and/or communicate the data via a network to a remote server. The implantable sensor includes an onboard power source, such as a battery, which powers the operations of the implantable sensor. The sensor may have a low power internal clock that is employed to cycle the operation of the sensor to reduce power consumption and extend battery life.

In accordance with an embodiment, a system is provided for collecting real-time on-demand measurements. The system includes an implantable sensor. The implantable sensor includes a power source, a sensing circuit, a communications circuit, a memory, and one or more processors. The sensing circuit is configured to sense a physiologic parameter of interest (PPOI) and to generate signals indicative of the PPOI. The communications circuit is configured to communicate with at least one of an implantable medical device (IMD) or an external device (ED). The memory is configured to store program instructions. The one or more processors are coupled to the memory. The program instructions are executable by the one or more processors to collect real-time on-demand measurements by activating the sensing circuit to generate the signals indicative of the PPOI, converting the signals to physiologic data indicative of the PPOI, storing the physiologic data in the memory, and directing the communications circuit to transmit the physiologic data to the at least one of the IMD or the ED.

Optionally, the communication circuit is configured to receive a data collection instruction, and the one or more processors are configured to perform the activating, converting, storing and directing operations in response to the data collection instruction in real-time on-demand. Optionally, the memory is configured to store the physiologic data over a collection period of time, and the one or more processors are configured to perform the directing operation to transmit the physiologic data in real-time at least one of i) on-demand upon request from at least one of the IMD or the ED, or ii) at a time according to a predetermined data transmission schedule.

Optionally, the system also includes the IMD. The IMD is configured to deliver a therapy and to modify at least one parameter of the therapy in response to receiving and analyzing the physiologic data from the implantable sensor. Optionally, the communications circuit is configured to communicate bidirectionally with the IMD through at least one of far field radio frequency wireless communication, conductive communication, or a direct wired connection.

Optionally, the power source is configured to store an amount of energy to supply the sensing circuit, the communications circuit, and the one or more processors for at least a predetermined number of data collection operations and communication sessions. The data collection operations and communication sessions are performed without any external energy delivery.

Optionally, the sensor includes a housing having a hermetically sealed interior cavity that holds the sensing circuit, the memory, the one or more processors, and the communications circuit. The communications circuit further includes a radiofrequency (RF) antenna provided within the interior cavity, and the housing is at least partially composed of a resistive material that is at least partially transparent to RF fields. The RF antenna may be at least one of i) a surface mount chip antenna, or ii) a conductive metallic trace arranged in a serpentine design. The RF antenna may be located on a printed circuit board or on an inner wall of the housing.

Optionally, the sensor includes a first housing portion at a first end of the sensor, a second housing portion at a second end of the sensor opposite the first end, and a flexible cable disposed between and connected to the first and second housing portions. The sensor includes a first electrode of the communications circuit held by the first housing portion and a second electrode of the communications circuit held by the second housing portion. The first electrode is electrically coupled to the second electrode via the flexible cable. The one or more processors are configured to direct the communications circuit to transmit the physiologic data by applying voltage bursts to the first and second electrodes to create a polarized electric field around the sensor.

Optionally, the one or more processors are configured to remain in a sleep mode until transitioning to a wake mode in response to receiving a wake-up instruction from a clock of the implantable sensor. The one or more processors are configured to perform at least one of the activating, converting, storing, and directing operations when in the wake mode. In the sleep mode, the power supply may be configured to supply power to the clock without supplying power to the one or more processors, the sensing circuit, or the communications circuit.

Optionally, the sensing circuit is configured to sense, as the PPOI, at least one of pressure, temperature, respiration, or a body generated analyte (BGA). The signals generated by the sensing circuit may represent electrical signals, for which at least one of voltage, current, capacitance, inductance or resistance varies based on a level of the PPOI.

Optionally, the power source includes a secondary battery that is electrically connected to one of (i) the IMD via a direct wired connection to receive electrical power from the IMD or (ii) an energy harvesting unit of the sensor. The energy harvesting unit includes a coil configured to inductively connect to an external recharge device to transfer electrical power from the external recharge device to the secondary battery via the energy harvesting unit.

In accordance with an embodiment, a method is provided for collecting real-time on-demand measurements. The method includes activating a sensing circuit of an implantable sensor to sense a physiologic parameter of interest (PPOI) and generate signals indicative of the PPOI. The sensing circuit is powered by a power source onboard the sensor. The method includes converting the signals to physiologic data indicative of the PPOI via one or more processors of the sensor, and storing the physiologic data in a memory of the sensor. The method also includes directing a communications circuit of the sensor to transmit the physiologic data to at least one of an implantable medical device (IMD) or an external device (ED).

Optionally, the physiologic data is transmitted to the IMD which delivers a therapy, and the method further comprises modifying at least one parameter of the therapy in response to receiving and analyzing the physiologic data from the communications circuit of the implantable sensor.

Optionally, converting the signals to the physiologic data includes digitizing the signals that are generated to form the physiologic data, and the directing of the communications circuit to transmit the physiologic data is in real-time in accordance with a predetermined schedule or on-demand in response to a request from at least one of the IMD or the ED.

Optionally, the method includes receiving a data collection instruction via the communications circuit. The activating, converting, storing, and directing operations are performed in real-time on-demand in response to receiving the data collection instruction. Optionally, the method includes determining a scheduled time according to a data transmission schedule stored in the memory. The activating, converting, storing, and directing operations are performed in real-time at the scheduled time.

Optionally, the method includes assembling the implantable sensor to include a first housing portion, a second housing portion, and a flexible cable disposed between and connected to the first and second housing portions. The assembling operation includes installing a first electrode of the communications circuit to the first housing portion, installing a second electrode of the communications circuit to the second housing portion, and electrically coupling the first electrode to the second electrode via the flexible cable. The directing operation to direct the communications circuit of the sensor to transmit the physiologic data includes applying voltage bursts to the first and second electrodes to create a polarized electric field around the sensor.

BRIEF DESCRIPTION OF THE DRAWINGS

FIG. 5 illustrates a perspective view of another example configuration for the implantable sensor formed in accordance with embodiments herein.

FIG. 6 is a flow chart of a method for intra-body communications from an implantable medical sensor according to an embodiment.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Figure 1:
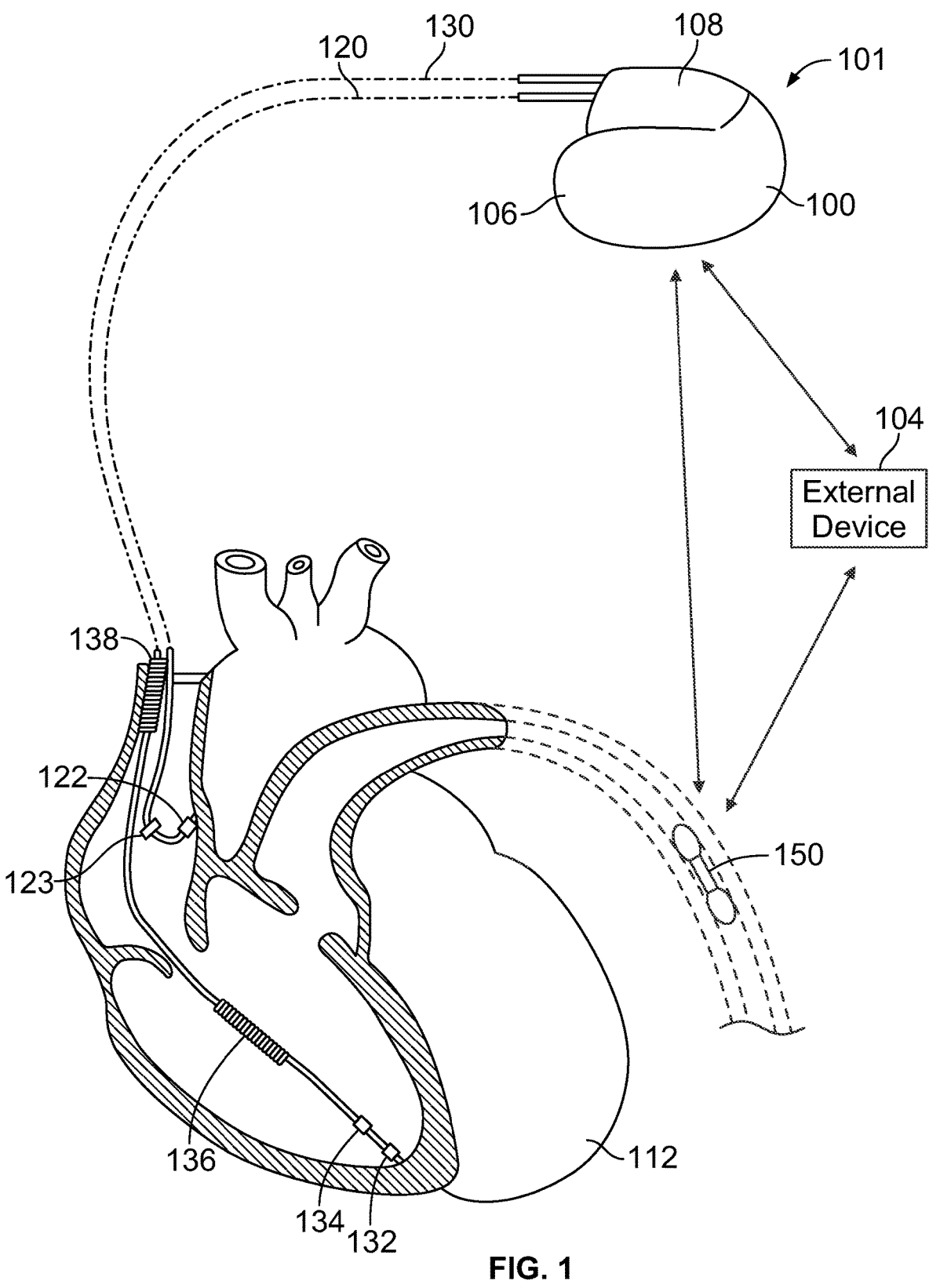
FIG. 1 illustrates a system that includes an implantable medical device (IMD), an implantable sensor, and an external device (ED) implemented in accordance with embodiments herein.

FIG. 1 illustrates a system 101 that includes an IMD 100, an implantable sensor 150, and an external device 104 implemented in accordance with embodiments herein. The IMD 100 and the implantable sensor 150 are implanted within the body of a patient. The external device 104 is outside of the patient body. The external device 104 may be a programmer, an external defibrillator, a workstation, a portable computer (e.g., laptop or tablet computer), a personal digital assistant, a cell phone (e.g., smartphone), a bedside monitor, and the like. The IMD 100 may represent a cardiac monitoring device, a pacemaker, a cardioverter, a cardiac rhythm management device, a defibrillator, a neurostimulator, a leadless monitoring device, a leadless pacemaker, and the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. Exemplary structures for the IMD 100 and the implantable sensor 150 are discussed and illustrated in the drawings herewith.

The IMD 100 includes a housing 106 that is joined to a header assembly 108 that holds receptacle connectors connected to a right ventricular lead 130 and an atrial lead 120, respectively. The atrial lead 120 includes a tip electrode 122 and a ring electrode 123. The right ventricular lead 130 includes an RV tip electrode 132, an RV ring electrode 134, an RV coil electrode 136, and an SVC coil electrode 138. The leads 120 and 130 detect intracardiac electrogram (IEGM) signals that are processed and analyzed as described herein, and also deliver therapies as described herein.

The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may further include a coronary sinus lead with left ventricular electrodes. The IMD 100 may provide full-function cardiac resynchronization therapy. Alternatively, the IMD 100 may be implemented with a reduced set of functions and components. For instance, the IMD may be implemented without ventricular sensing and pacing.

The implantable sensor 150 is configured to be implanted at a location remote from the electrodes of the leads 120 and 130. The implantable sensor 150 may be implanted in a blood vessel, such as an artery or vein. In an embodiment, the sensor 150 is implanted within the pulmonary artery (PA). The sensor 150 may be anchored to the vessel wall of a blood vessel using one or more expandable loop wires. The diameter of each loop should be larger than the diameter of target blood vessel in order to provide adequate anchoring force. Optionally, instead of the loop wire, the sensor 150 may be attached to the end of a self-expandable stent and deployed into the blood vessel through a minimally invasive method. This method may be preferable over the loop wire(s) in situations in which strong anchoring is needed.

Alternatively, the implantable sensor 150 may be secured to tissue outside of blood vessels. The sensor 150 may be secured in place by using a fixation screw (e.g., helix)

attached to the housing. The screw may anchor the sensor 150 to patient heart tissue, such as cardiac tissue of the left or right ventricle. The sensor 150 is configured to sense a physiologic parameter of interest (PPOI) and to generate signals indicative of the PPOI. In a non-limiting example, when the sensor 150 is disposed within the PA, the sensor 150 may sense, as the PPOI, blood pressure.

Figure 2:
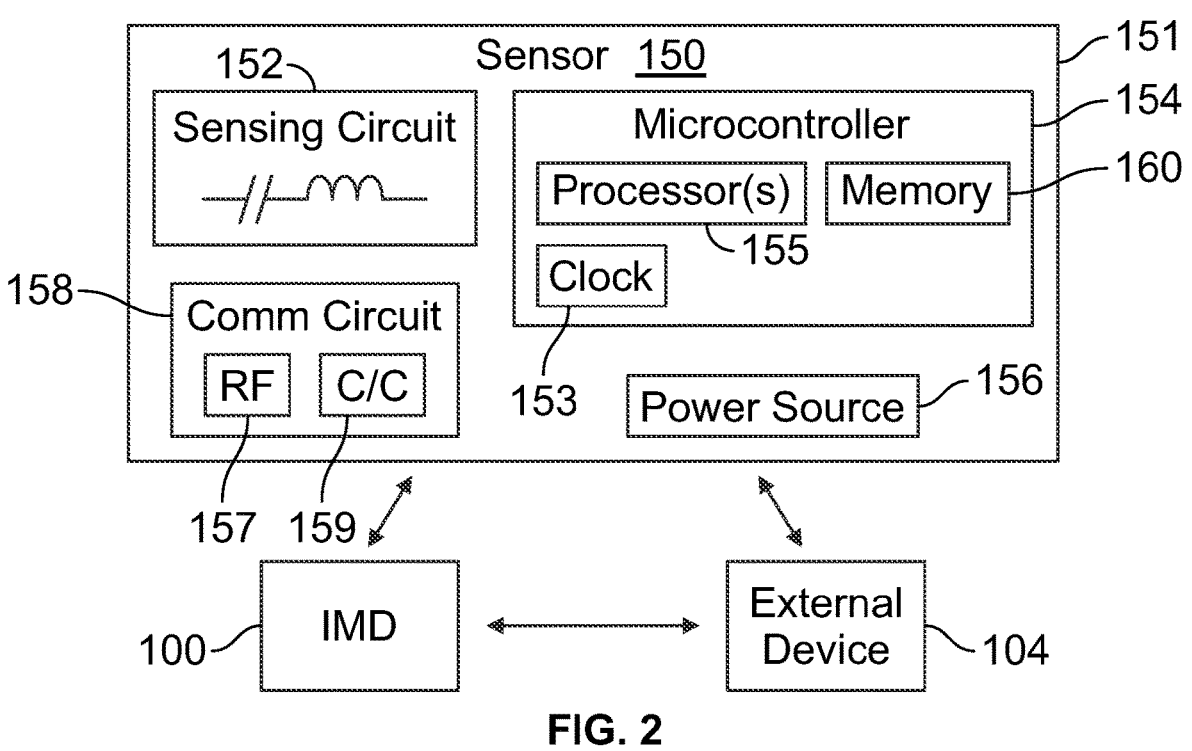
FIG. 2 illustrates a block diagram of the system formed in accordance with embodiments herein, showing components of the implantable sensor.

FIG. 2 illustrates a block diagram of the system 101 formed in accordance with embodiments herein, showing components of the implantable sensor 150. The sensor 150 comprises a sensing circuit 152, a controller 154, a power source 156, a communications circuit 158 and a memory 160. The controller 154 includes one or more processors 155. The one or more processors 155 are operably coupled to the memory 160. The sensor 150 includes a housing 151 that holds and encapsulates the sensing circuit 152, the controller 154, the power source 156, the communications circuit 158, and the memory 160, to protect these components from the harsh organic environment of the body. The housing 151 may be hermetically sealed.

The sensing circuit 152 is configured to sense a physiologic parameter of interest (PPOI) and to generate signals indicative of the PPOI. The sensing circuit 152 is configured to sense, as the PPOI, at least one of pressure (e.g., blood pressure), cardiac output, temperature, respiration, or a body generated analyte (BGA) (e.g., blood glucose level). The signals generated by the sensing circuit 152 represent electrical signals. Electrical parameters of the signals, such as voltage, current, capacitance, inductance or resistance, may vary based on a level of the PPOI. The sensing circuit 152 includes one or more sensing elements that sense the PPOI, and circuitry that generates the electrical signals indicative of the PPOI. In an embodiment, the sensing circuit may include elements such as amplifiers and analog-to-digital converters. The elements of the sensing circuit may create a representation of the PPOI that can be read by the microcontroller.

The controller 154 may be implemented as a microcontroller unit or another processor configuration. The controller 154 performs at least some of the operations described herein to collect real-time on-demand measurements by generating physiologic data and communicating the physiologic data to at least a second device, without requiring patient interaction or external energy delivery at the time of data generation and communication. The controller 154 represents hardware circuitry that includes and/or is connected with the one or more processors 155 (e.g., one or more microprocessors, integrated circuits, field programmable gate arrays, etc.).

The controller 154 includes and/or is connected with the memory 160, which is a tangible and non-transitory computer-readable storage medium. The memory 160 stores program instructions (e.g., software) that is executed by the one or more processors 155 to perform the operations of the sensor 150 described herein. The memory 160 additionally may store different information, such as the physiologic data that is generated by the sensing circuit 152. The memory 160 may store the physiologic data until the sensor 150 transmits the physiologic data to the IMD 100 and/or the ED 104.

In an embodiment, the controller 154 includes and/or is connected with an internal clock 153 or timer. The clock 153 may be used to cycle the sensor 150 between wake and sleep modes to conserve electrical energy. The controller 154 may refer to the clock 153 to determine when to activate the sensing circuit 152 to generate the signals indicative of the PPOI according to a data collection schedule. For example, if the data collection schedule in the memory 160 indicates that new physiologic data should be generated at a specific time (e.g., 6 AM) of the current day, then the controller 154 can utilize the clock 153 to determine when it is the specific time to activate the sensing circuit 152 according to the schedule, such that the physiologic data is generated and collected in real-time at specific prescribed times.

The communications circuit 158 is operably connected to the controller 154 via conductive elements. The communications circuit 158 communicates with the IMD 100 and/or the ED 104. The communications circuit 158 may be communicatively connected to the IMD 100 via an intra-body bidirectional link, which enables the sensor 150 to transmit information (e.g., data) to the IMD 100 and receive information from the IMD 100. The communications circuit 158 may include an RF module 157 and/or a conductive communication module 159. The RF module 157 includes an antenna for sending and receiving RF signals. The conductive communication module 159 includes at least two spaced-apart electrodes, connected via a conductive wire or cable, that are powered to create a polarized electric field around the sensor 150, as described herein with reference to FIG. 5.

The power source 156 supplies electrical energy to power the operations of the sensor 150. The power source 156 may include one or more secondary (e.g., rechargeable) batteries, one or more primary batteries, one or more capacitors, and/or associated circuitry, such as inductive coils, charging circuits, and the like.

In operation, the controller 154 may directly convert, or manage conversion of, the signals from the sensing circuit 152 to digital physiologic data. The controller 154 may execute the program instructions stored in the memory 160 to activate the sensing circuit to generate the signals indicative of the PPOI. The controller 154 may activate the sensing circuit 152 on-demand in response to receiving a request (e.g., a data collection instruction) from another device or at a prescribed time according to a schedule stored in the memory 160. The controller 154 also executes the program instructions to convert the signals from the sensing circuit 152 to physiologic data indicative of the PPOI. After converting, the controller 154 stores the physiologic data in the memory 160. In an embodiment, the controller 154 (e.g., the one or more processors 155 thereof) are configured to digitize the signals generated by the sensing circuit to form the physiologic data.

The controller 154 then directs the communications circuit 158 to transmit at least some of the physiologic data stored in the memory 160 to the IMD 100 and/or the ED 104. For example, the memory 160 may store the physiologic data that is recently converted and digitized until the controller 154 directs the communications circuit 158 to transmit the physiologic data. The communications circuit 158 may be directed to transmit the data in real-time in accordance with a predetermined schedule or on-demand in response to a request from at least one of the IMD or the ED. For example, the transmission may be triggered by a stimulus, which may be a determination that it is time for a scheduled data transmission, a receipt of an impromptu, on-demand request from the IMD 100 and/or the ED 104, a determination by the controller 154 that the PPOI has crossed a threshold value or has changed more than a threshold rate or extent, or the like. The communications of the physiologic data may be controlled according to a predetermined schedule, a request, and/or a detected exceptional value or trend in the measured PPOI.

In an embodiment, the IMD 100 is utilized as a bridge component to relay communications between the sensor 150 and the ED 104. For example, the controller 154 may use the communication circuit 158 to transmit a message within the body of the patient to the IMD 100. Upon receipt, the IMD 100 may retransmit the message (or generate a new message that includes the content of the received message) to the ED 104. The IMD 100 may also relay messages received from the ED 104 to the sensor 150. Optionally, the sensor 150 may have sufficient onboard power to communicate information to the ED 104 and/or receive information from the ED 104 without utilizing the IMD 100 as a relay.

In an embodiment for pressure sensors, the ED 104 includes an atmospheric pressure gauge that monitors atmospheric pressure either periodically or on-demand. The sensor 150 produces pressure data along with a time stamp, or time synchronized relative to ED 104 or IMD 100. The on-demand or time-stamped atmospheric pressure measurement of ED 104 can be used to convert time-stamped or time synchronized absolute blood pressure measured by the sensor 150 to relative blood pressure, upon time-synchronization between the sensor 150 and the ED 104. For example, to help with time-synchronization, the ED 104 can instruct the sensor 150 or IMD 100 to collect the pressure data when the patient is near-by the ED 150. In another example, the pressure measurement time of sensor 150 and ED 104 can be pre-scheduled relative to the sleep schedule of the patient (e.g., 3 AM), to reduce the variability of blood pressure measurements attributable to changes in patient posture.

In accordance with embodiments described herein, the intra-body communication between the sensor 150 and the IMD 100 provides various benefits. For example, the PPOI is measured by the sensor 150 and the physiologic data is transferred to the IMD 100. The IMD 100 may provide a treatment for the patient. When the IMD 100 is a CRT/pacemaker, the treatment may be stimulation therapy. When the IMD 100 is an implantable glucose dispenser, the treatment may be a dose of insulin. Communication between the IMD 100 and the sensor 150 enables autonomous and prompt adjustment of treatment parameters based on real-time feedback from the PPOI. For example, in response to a change in the PPOI, the system 101 enables quicker modification of the treatment parameters provided by the IMD 100 than a conventional system that requires the patient to periodically activate the sensor via an external energy source. The earlier adoption of a modified treatment improves patient outcome because the treatment is tailored and timely for the current patient conditions.

The IMD 100 is able to timely modify the treatment parameters because the sensor 150 may autonomously collect and communicate updated, real-time physiologic data. The data collection and communication may occur more often and/or with less delay after a change in the PPOI than relying on patient interaction to activate the sensor. For example, the sensor 150 may collect measurements and transmit the physiologic data on a schedule that is more reliable and/or more frequent than schedules that rely on patient involvement. Furthermore, the treatment parameters may be quickly modified because the sensor 150 can autonomously provide on-demand updates to the IMD 100 and/or ED 104. Thus, instead of requiring the ED 104 or another device to prompt the patient or another person to activate the sensor for acquiring an updated measurement, the IMD 100 and/or ED 104 can simply communicate a request or instruction to the sensor 150 whenever the requesting device desires updated physiologic data, and the sensor 150 responds with a real-time update. Optionally, the sensor 150 may also provide unsolicited and unscheduled updates to the IMD 100 and/or ED 104 in certain situations. For example, the sensor 150 may collect and store data measurements at a greater frequency than the data is typically transmitted to the IMD 100 and/or ED 104. Optionally, the controller 154 may monitor the PPOI over time and determine when a value of the PPOI crosses a designated threshold and/or changes at a rate or extent that is outside of an expected rate or extent of change. In response to making this determination, the sensor 150 may notify the IMD 100 and/or ED 104, even if the notification occurs outside of a scheduled communication session and is not prompted by a received request for updated physiologic data, and provides the IMD 100 and/or the ED 104 early access to information that could require a medical response, thereby improving the patient outcome.

The intra-body communication also overcomes difficulties with prior implantable sensors, the size of which was limited due to the target implant locations, such as blood vessels. The size constraints limited the size of the batteries and other energy sources onboard the sensor, which also limits the energy storage capability. The limited energy storage in prior sensors limited the operational lifespan of the sensors (at least between charging sessions), and also limited the distance that the sensor could communicate, which created problems for direct communication to the external device such as a bedside monitoring device. In accordance with at least some embodiments herein, these issues are addressed by energy conservation and the use of the IMD 100 as a bridge or relay communication device between the sensor 150 and the ED 104. For example, the physiologic data from the sensor 150 is sent to the IMD 100, which has an established communication link with the ED 104. The implantable sensor 150 according to embodiments herein is implemented in a small form factor to retain the ability to implant the sensor 150 in narrow locations, such as blood vessels. The sensor 150 can increase reliability and consistency of physiologic data collection by autonomously collecting physiologic data, independent of patient interaction, which promotes a better patient outcome.

Figure 3A:
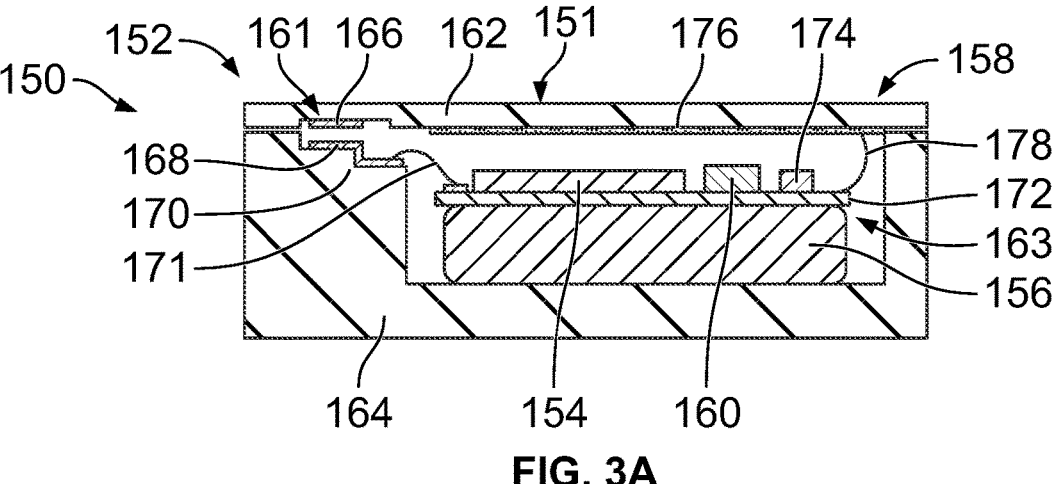
FIG. 3a illustrates a side cross-sectional view of one example configuration for the implantable sensor formed in accordance with embodiments herein.

FIG. 3a illustrates a side cross-sectional view of one example configuration for the implantable sensor 150 formed in accordance with embodiments herein. In the illustrated embodiment, the sensing circuit 152 includes a parallel-plate pressure-sensitive capacitor 161. The capacitor 161 includes a first capacitor plate 166 and a second capacitor plate 168 that are parallel and spaced apart from one other by a predetermined distance. The plates 166, 168 are electrodes. The first capacitor plate 166 may be mounted to a lower surface of a first portion of the housing 151, and the second capacitor plate 168 is mounted to an upper surface of a second portion of the housing 151. In the illustrated embodiment, the housing 151 is defined by an upper wafer 162 and a lower wafer 164 that couple together to define and enclose an interior cavity 163. The first capacitor plate 166 is disposed on the upper wafer 162, and the second capacitor plate 168 is mounted on a shelf 170 of the lower wafer 164. The shelf 170 is spaced a predetermined distance from the lower surface of the upper wafer 162 to space the first and second capacitor plates 166, 168 a predetermined distance from one another. The upper wafer 162 and the lower wafer 164 may be composed of a dielectric material. The upper and lower wafers 162, 164 are fused together to form a monolithic housing that seals the components within the interior cavity 163 from the harsh biological environment outside of the housing 151. The housing 151 may be flexible. For example, a portion of the upper wafer 162 may have a pressure sensitive deflective region underlying at least a portion of the first capacitor plate 166, whereby the deflective region deflects in response to changes in ambient pressure in the medium in which the sensor 150 is disposed.

A conductive element 171, such as a gold wire, is electrically connected to the second capacitor plate 168 and extends from the second capacitor plate 168 to a printed circuit board (PCB) 172 of the sensor 150. The controller 154 is disposed on the PCB 172. The conductive element 171 electrically connects the second capacitor plate 168 to the PCB 172 to conduct signals indicative of the PPOI to the controller 154. The conductive element 171 may be flexible. Alternatively, the conductive element 171 may be inflexible. The sensing circuit 152 may include an inductor formed from one or more windings of a conductive material. The inductor may be electrically coupled to one of the first and second capacitor plates 166, 168.

In the illustrated embodiment, the PCB 172 is connected to the power source 156, which may be a battery. The memory 160 is disposed on the PCB 172 along with a surface mount resistor or capacitor 174.

Figure 3B:
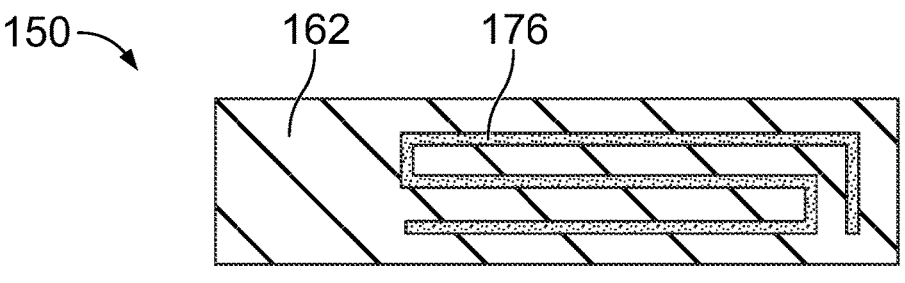
FIG. 3b illustrates a top-down view of the sensor according to an embodiment.

In the illustrated embodiment, the sensor 150 includes an antenna 176 which represents a component of the communications circuit 158. More specifically, the antenna 176 is a component of the RF module 157 (shown in FIG. 2), and the antenna 176 is used to send and receive RF wireless communication signals. The antenna 176 is mounted on the upper wafer 162 (e.g., lid or upper housing portion) in the illustrated embodiment. FIG. 3b illustrates a top-down view of the sensor 150 according to an embodiment. The antenna 176 is shown as a conductive metallic trace arranged in a serpentine design of connected linear line segments. The antenna 176 may have another shape, such as spiral, in another embodiment. The size, design, and placement of the antenna 176 optionally may be selected to cause the antenna 176 to resonate at a predetermined target communication frequency, to increase the transmission efficiency and output amplitude relative to the antenna not resonating at the target communication frequency.

The antenna 176 in FIG. 3a is secured to an inner surface or wall of the upper wafer 162 that faces towards the interior cavity 163 and the lower wafer 164. As such, the antenna 176 is within the interior cavity 163. The upper wafer 162 may be at least partially translucent to enable viewing the antenna 176 through the upper wafer 162 in the top-down view of FIG. 3b. In an alternative embodiment, the antenna 176 may be disposed on an inner surface or wall of the lower wafer 164, integrated within the housing 151 itself such as within a thickness of the upper wafer 162, or disposed on an outer (e.g., exterior) surface of the upper wafer 162. For example, the antenna 176 may be a ceramic antenna that is sandwiched (or embedded) between layers of the housing 151, such as within the thickness of the upper wafer 162 or the thickness of the lower wafer 164.

The antenna 176 is electrically connected to the PCB 172 via a second conductive element 178. The second conductive element 178 may be similar to the conductive element 171. For example, the second conductive element 178 may be a gold wire or another flexible element. The controller 154 may communicate the physiologic data to the IMD 100 and/or the ED 104 by generating a message that is conveyed via the second conductive element 178 to the antenna 176 and emitted by the antenna 176 as an RF communication. The antenna 176 also receives RF messages and conveys the received messages to the controller 154 for analysis. The housing 151 may be at least partially composed of an electrically resistive material that is at least partially transparent to RF fields. The RF signals may propagate through the upper wafer 162 with insubstantial interference or loss. The electrically resistive material of the housing 151 may be glass, fused silica, ceramic, resistive metals, silicone, and the like.

The size of the antenna structure may be designed to be a fraction of a wavelength of the target communication frequency (ex, ½ or ¼ or ⅛ and etc. of wavelength) or integer multiples of wavelength (1×, 2× or 3× and etc. of wavelength) in order to efficiently broadcast and receive a signal. In order to increase the electrical size of the antenna within the limited physical size of the sensor 150 (i.e. to increase antenna efficiency), the antenna conductive traces may be covered by high dielectric materials. This changes the effective wavelength of the antenna. Encompassing the conductive traces in layers of high dielectric will greatly enhance the effective wavelength thus making the antenna more efficient at the frequency of interest. Although the antenna 176 is a conductive metallic trace in the illustrated embodiment, the antenna may be a surface mount chip antenna, or conductive traces patterned directly on the PCB 172 to resonate at the frequency of interest, in alternative embodiments.

Optionally, the RF module 157 (shown in FIG. 2) of the communication circuit 158 may utilize a communication protocol such as Bluetooth low-energy (BLE). The BLE protocol also has the advantage that the physiologic data can be shared with cell phones, tablets and other consumer computer devices that are Bluetooth enabled without converting formats. Alternatively, lower frequency RF communication, such as 400 MHz MICS, or other frequencies bands in the ISM could be used to communicate to other sensors or devices.

Figure 4A:
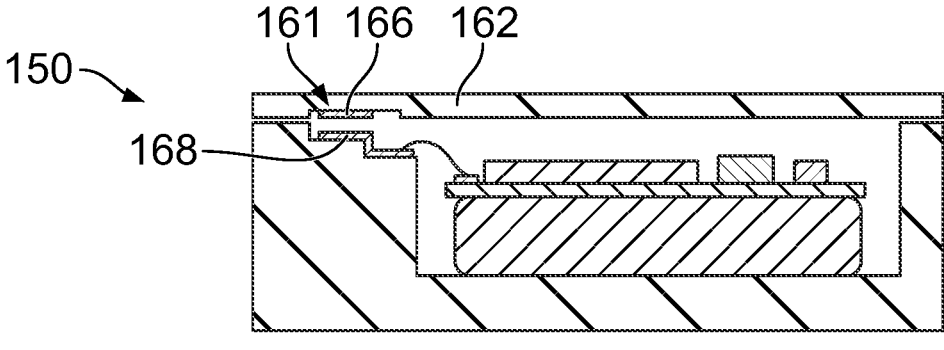
FIG. 4a illustrates a side cross-sectional view of another example configuration for the implantable sensor formed in accordance with embodiments herein

FIG. 4a illustrates a side cross-sectional view of another example configuration for the implantable sensor 150 formed in accordance with embodiments herein. The sensor 150 in FIG. 4a only differs from the sensor 150 in FIGS. 3a and 3b with respect to the communications circuit 158. The sensor 150 utilizes RF wireless communication with the IMD 100 and/or ED 104 without the presence of the discrete antenna 176 shown in FIGS. 3a and 3b. For example, there is no discrete antenna mounted to the upper wafer 162. Instead, one or more existing conductive sensing elements of the sensor 150 are utilized as an antenna to send and receive RF signals.

In the illustrated embodiment, one or both of the capacitor plates 166, 168 of the parallel-plate pressure-sensitive capacitor 161 function as an antenna. The capacitor plate(s) 166, 168 may be designed to resonate at a predetermined target communication frequency. The capacitor 161 still performs the PPOI sensing. As a result, the capacitor 161 represents a component of both the sensing circuit 152 and the communications circuit 158. Within the sensing circuit 152, the capacitor 161 may function as a pressure sensing element.

Figure 4B:
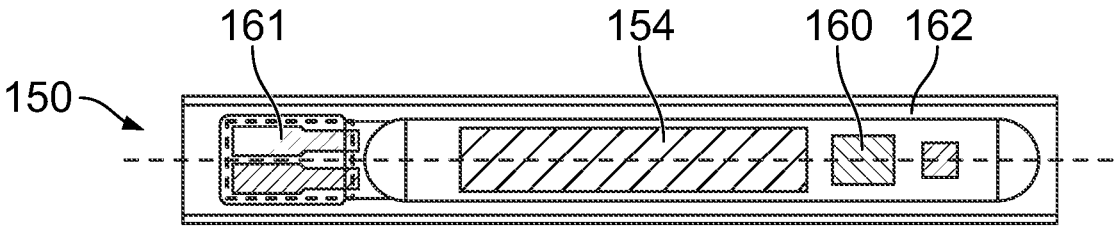
FIG. 4*b* is a top-down view of the implantable sensor shown in FIG. 4*a* according to an embodiment.

FIG. 4b is a top-down view of the implantable sensor 150 shown in FIG. 4a according to an embodiment. Without the presence of the antenna 176, the controller 154 and the memory 160 are visible through the light transmissible (e.g., translucent) upper wafer 162.

Figure 4C:
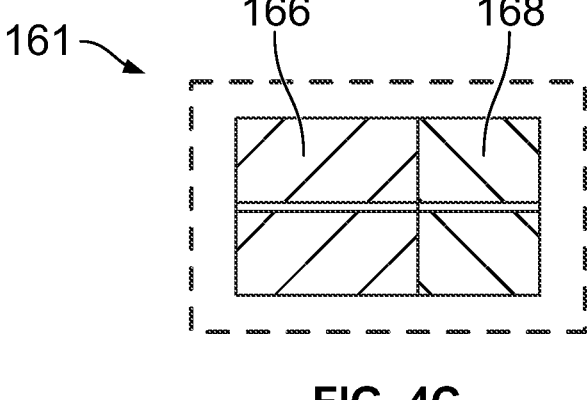
FIG. 4*c* is an enlarged top-down view of the parallel-plate pressure-sensitive capacitor according to an embodiment.

FIG. 4c is an enlarged top-down view of the parallel-plate pressure-sensitive capacitor 161 according to an embodiment. The capacitor plates 166, 168 are stacked vertically, such that the first or upper plate 166 is above and at least partially overlaps the second or lower plate 168. The plates 166, 168 may be on the order of 0.5 to 3.5 mm in one dimension and 1 to 6 mm in a second dimension that is orthogonal to the first dimension. Optionally, the second or lower plate 168 may have a greater surface area than the first or upper plate 166.

In an alternative embodiment, the housing may be composed at least partially of an electrically conductive material that can cause undesired shielding and interference, effectively blocking the RF field. In such an embodiment, the sensor 150 may include a hermetic electrical feed-through that extends through the conductive housing from the controller and/or PCB within the interior cavity to an antenna external to the sensor housing. In this case, conductive objects used to affix the sensor to the patient tissue, such as one or more wire loops, may be used as antenna elements. During use, an RF signal from inside the sensor may be conveyed to the external antenna element via the electrical feed-through. The wire loop or loops may be electrically insulated to reduce antenna loss due to electrical loading of conductive organic liquid such as blood.

FIG. 5 illustrates a perspective view of another example configuration for the implantable sensor 150 formed in accordance with embodiments herein. The sensor 150 in the illustrated embodiment uses the conductive communication module 159 (shown in FIG. 2) of the communications circuit 158 to communicate with the IMD 100. The conductive communication of physiologic data utilizes at least two exposed electrodes that are spaced apart from one another to create a polarized electric field around the sensor 150, and the physiologic data is transmitted via the electric field. Optionally IMD 100 is used as a link to relay information received from the sensor 150 to the ED 104.

The sensor 150 has an elongated, barbell shape in the illustrated embodiment. For example, the sensor 150 includes a first housing portion 180 at a first end 182 of the sensor 150, a second housing portion 184 at a second end 186 of the sensor 150 opposite the first end 182, and a narrow intermediate segment disposed between and connected to the first and second housing portions 180, 184. The intermediate segment may be defined by a flexible cable 188. The communications circuit 158 includes a first electrode 190 held by the first housing portion 180 and a second electrode 192 held by the second housing portion 184. The first electrode 190 is electrically coupled to the second electrode 192 via the flexible cable 188, which includes one or more insulated conductors (e.g., wires). The other components of the sensor 150 that are shown and described with reference to FIG. 3a, other than the antenna 176, may be contained within one or both of the housing portions 180, 184. The components may be distributed between the two housing portions 180, 184. In one example, the power source 156 is disposed within the first housing portion 180. The second housing portion 184 may contain the sensing circuit 152 (e.g., parallel-plate capacitor 161) and the electronics on the PCB 172, including the controller 154 and the memory 160.

The electrodes 190, 192 are exposed to the organic environment of the patient, such that patient tissue and/or fluid physically contacts the electrodes 190, 192. The sensor 150 transmits the digital physiologic data by applying voltage bursts to the two electrodes 190, 192, which creates polarized electric field around the implanted sensor 150. The voltage bursts may be one or more series of short bursts. The bursts may be powered by the power source 156, such as a battery. The IMD 100 within the patient may receive this electric field, that is based on the bursts, using existing leads 120, 130 or electrodes (e.g., 122, 123, 132, 134, 136, 138 in FIG. 1) exposed to the body. Since the data transmission is based on the short bursts of pulse voltage with a negligible current, the power consumption for the sensor 150 is minimal. The bursts may be on the order of microseconds. The IMD 100 may receive the transmitted physiologic data through an existing cardiac monitoring channel by sensing the polarized electric field generated by the electrodes 190, 192. Additional information about conductive communication is described in U.S. Pat. No. 9,168,383, which is incorporated by reference herein.

Because the electrodes 190, 192 are exposed to the organic material of the patient, the electrodes 190, 192 are composed at least partially of a biocompatible and corrosion-resistant material. The electrode material may include one or more metals, such as platinum, platinum-iridium, titanium, MP35N (e.g., an alloy of nickel, cobalt, chromium, and molybdenum), and/or the like.

The flexible cable 188 lengthens the separation distance between the two electrodes 190, 192, which improves data delivery performance. The separation distance between the first electrode 190 and the second electrode 192 may be at least 0.5 inches. For example, the separation distance may be at least 0.5 inches and no greater than 3 inches. Increasing the separation distance between the electrodes 190, 192 to at least 0.5 inches can increase the performance and efficiency of the intra-device communications. For example, an increase in the separation distance may provide a bump in the amplitude or energy level of the electric field located father away from sensor without increasing the power consumption of the sensor 150, thereby increasing communication distance between the sensor 150 and the IMD 100. The flexible cable 188 is used to achieve this separation while enabling the deliverability of the sensor 150 during implant using a conventional catheterization process. The cable length of the cable 188 can be adjusted depending on the energy budget of the power source 156. In an alternate embodiment, the housing portions 180 and 184 can be combined into a single housing. In this case, one end of the cable 188 is electrically connected to the combined single housing that includes the electrode 192 in one end, and the other end of the cable 188 is terminated with the electrode 190. This arrangement still provides separation between two electrodes for efficient communication.

In an alternative embodiment, instead of using wireless communication, the sensor 150 may have a direct wired connection to the IMD 100. For example, the sensor 150 can be connected directly to other implantable medical devices via one or more wires. A first wire may provide power and data communication, and a second wire may provide the return path. Alternatively, the one wire could be used with one conductive electrode (e.g., 190 or 192) on each of the sensor 150 and the IMD 100. In this case the electrode would serve as either the return path or the power/data communication path.

Reference is now made to the power source 156 shown in FIGS. 2 and 3a which powers the operations of the sensor 150, such as data generation and transmission. In one embodiment, the power source 156 includes at least one primary battery. The primary battery may have sufficient energy density and charge capacity to support the lifetime of the sensor 150, particularly if actions are taken to conserve power consumption, as described below. The primary battery may have an electrochemical composition that includes lithium ion or lithium monofluoride (CFx).

In another embodiment, the power source 156 includes at least one secondary or rechargeable battery. When the secondary battery is at least partially depleted, external power can be used to charge the secondary battery. For example, the controller 154 may determine, based on electrical sensor data, when the remaining charge stored within the battery drops to or beyond a preset low voltage or energy threshold. In response, the controller 154 may communicate a notification to the IMD 100 and/or the ED 104 that a recharge session for the sensor 150 is necessary.

In a first example, the power source 156 includes an energy harvesting unit in conjunction with the secondary battery and used to support recharge of the secondary battery. The energy harvesting unit includes a coil. The coil inductively connects to an external recharge device to transfer electrical power (e.g., electric current) from the external recharge device to the secondary battery via the energy harvesting unit. The external recharge device may include an external device coil that provides power. The energy harvesting unit may include AC-DC rectification with an optional voltage multiplier electrically coupled to the battery. To support the extended recharge process time of a few mins to hours, for non-direct wired systems, the external recharge coil can be configured in the form of the body pads, a patch taped to the surface of body or a wearable vest/band/belts. Once charged, the secondary battery stores a sufficient amount of energy to successfully supply power to the sensing circuit 152, the controller 154, and the communications circuit 158 for at least a predetermined number, greater than one, of data collection operations and communication sessions. As a result, the data collection operations and communication sessions are performed by the sensor 150 between recharge sessions, without any patient interaction or external energy delivery. The predetermined number may be in the hundreds or thousands.

In the embodiment described above in which the sensor 150 has a direct wired connection to the IMD 100, the at least one secondary battery of the sensor 150 can recharge by receiving electrical energy directly from the IMD 100. The IMD 100 is larger than the sensor 150 and may store more electrical energy onboard than the sensor 150. The IMD 100 may have sufficient electrical energy to power the operations of the IMD 100 as well as recharge the secondary battery of the sensor 150. The IMD 100 may periodically send power to the sensor 150 from its own power source, usually a primary battery, to keep the sensor 150 active. The recharge session may take place over the same communication lines as the data communication.

The secondary batteries may have an electrochemical composition that includes lithium ion, lithium ion polymer (Li-poly), or the like. Optionally, the batteries may be or include thin film batteries that can be fabricated in a planar process.

In order to extend the operational lifetime of the sensor 150, the controller 154 operates the sensor 150 according to a scheme designed to limit power consumption and conserve charge. For example, the sensor 150 performs data collection operations and communication sessions. During a data collection operation, the sensing circuit 152 senses the PPOI and generates the signals indicative of the PPOI. The controller 154 may digitize the signals generated by the sensing circuit 152 to form the physiologic data, and then store the digital physiologic data in the memory 160. The signals that are stored for each data collection operation represent the physiologic data generated over a collection period of time. During the communication session, the communications circuit 158 is controlled to transmit the physiologic data from the memory 160 to the IMD 100 and/or the ED 104. Both the data collection and communication operations require power from the power source 156.

In an embodiment, the controller 154 conserves power by limiting the performance of each of the data collection operations and communication sessions to designated times according to predetermined schedules and/or requests received from authorized devices, such as the IMD 100 and/or the ED 104. The data collection operation refers to collecting real-time on-demand measurements, and includes activating the sensing circuit 152 to generate the signals indicative of the PPOI, converting the signals to physiologic data indicative of the PPOI, and storing the physiologic data in the memory 160. The communication session refers to directing the communications circuit 158 to transmit at least some of the physiologic data stored in the memory 160 to the IMD 100 and/or ED 104. The memory 160 may store a data collection schedule that identifies specific times at which the data collection operation should be performed, or a designated interval or frequency between data collection operations. The memory 160 may also store a data transmission schedule that identifies specific times at which the stored data should be communicated to the IMD 100 and/or the ED 104, or a designated interval or frequency between communication sessions. The controller 154 may abide by the schedules based on the low power clock 153. For example, absent a specific on-demand request for data collection or transmission or a detection by the controller 154 in real-time that the value of the PPOI is outside of a preferred range, the controller 154 may use the clock 153 to only perform the data collection operations and/or the communication sessions at the times specified in the predetermined schedules.

In an embodiment, the data collection operations may be scheduled to occur more frequently than the communication sessions. As such, after a first communication session in which the data stored in the memory 160 is extracted and transmitted, several data collection operations may occur before the subsequent, second communication session in the data transmission schedule. The data may aggregate in the memory 160 over a collection period of time until it is time for the next communication session or a transmission request is received from the IMD 100 and/or ED 104.

The other stimulus for performing the data collection operation and/or the communication session is receipt of a specific request for an on-demand update. For example, the sensor 150 may receive a data collection instruction from the IMD 100 or the ED 104. In response to receiving a data transmission instruction, the controller 154 retrieves physiologic data from the memory 160 and transmits the physiologic data, via the communications circuit 158 to the IMD 100 and/or ED 104. Optionally, the controller 154 may perform a data collection operation to generate new physiologic data, and then store the new physiologic data in the memory 160, even if it is not yet time to collect new data according to the schedule. The physiologic data that is retrieved from the memory 160 includes the new physiologic data that is generated after receiving the data collection instruction. The controller 154 directs the communications circuit 158 to transmit the new physiologic data to the IMD 100 and/or ED 104 responsive to the data collection instruction, such that the requesting device receives updated measurements in real-time and on-demand, without requiring human interaction or an external energy transfer to the sensor 150 between the time at which the instruction is received and the time at which the new physiologic data is transmitted.

To reduce power consumption and increase the longevity of the implantable sensor 150, the low power clock 153 can be used to cycle the sensor 150 between wake and sleep modes of operation. In the sleep mode, most of the components of the sensor 150 are inactive and draw little to no power from the power source 156. For example, the power source 156 may only supply power to the clock 153, which is a low power device. The one or more processors 155, the sensing circuit 152, and/or the communications circuit 158 may not receive power from the power source 156 during the sleep mode. The clock 153 may provide a wake-up instruction to the one or more processors 155 and other components, for transitioning the sensor 150 to the wake mode, in response to determining that it is a scheduled time to perform a data collection operation and/or a communication session. Even in the sleep mode, the communications circuit 158 may be configured to sense and receive messages, such as requests to collect data and/or transmit data. The sensor 150 transitions to the wake mode in response to receiving and verifying the receipt of such a request. After performing the scheduled and/or requested tasks, the sensor 150 may return to the sleep mode.

The implantable sensor can be in the low power sleep mode for most of the time, while only the timer (e.g., clock 153) is running to wake-up the controller 154 in the predetermined time interval. In this scheme, the operational duration and occurrence of relatively power-demanding activities is reduced to extend energy storage life.

Optionally, the operating schedule of the sensor 150 may be synchronized to a schedule of the IMD 100 and/or ED 104 that communicates with the sensor 150 to reduce system-wide power consumption. For example, internal timing intervals in the devices may be synced so that the communication session of the sensor 150 may occur at a common time period as the listening for data signals from a communication device onboard the IMD 100. As a result, the communication function in both sides is enabled only for a short amount of time, such as at a designated frequency per day according to a predetermined schedule. The overall energy consumption of the system 101 can be reduced through this synchronization.

When the IMD 100 receives the physiologic data from the sensor 150, the IMD 100 analyzes the data. If the data indicates a change in a physiologic parameter or condition that is outside of a designated range, then the IMD 100 may modify at least one setting or characteristic of a therapy delivered to the patient based on the change. For example, the IMD 100 may modify the therapy by increasing or decreasing an amplitude or frequency of stimulation pulses administered to the patient. The IMD 100 may also modify therapy by switching to defibrillation shock therapy from pacing therapy, or vice-versa.

FIG. 6 is a flow chart 200 of a method for intra-body communications from an implantable medical sensor according to an embodiment. The method may include additional steps than shown in FIG. 6, fewer steps than shown in FIG. 6, and/or different steps than shown in FIG. 6. Furthermore, the order of the steps presented in FIG. 6 is not a limitation unless one step is specifically described as following or based on another step.

Referring to FIGS. 1 through 5, the method begins at 202, where the implantable sensor is active to collect real-time on-demand measurements. The sensor is active to collect the measurements without any patient action or intervention. The measurements are collected in real-time contemporaneous with normal or abnormal episode occurrences (e.g., a sinus rhythm or an arrhythmia). The sensor operates on-demand, in that the sensor activates the measurement operation without patient action or intervention. For example, the sensor may be activated by a data collection instruction received from the IMD or ED. Additionally or alternatively, the sensor may be activated based on a data collection schedule. The data collection schedule may be stored in the sensor, in the IMD or in the ED. At 202, the controller 154 activates a sensing circuit 152 of the implantable sensor 150 to collect the real-time on-demand measurements. Specifically, the sensing circuit 152 is activated to sense a physiologic parameter of interest (PPOI). The sensing circuit 152 is powered by a power source 156 onboard the sensor 150. The PPOI may be pressure, temperature, respiration, a BGA, or the like.

At 204, signals indicative of the PPOI are generated. The signals may be generated by the sensing circuit 152. The sensing circuit 152 may include a parallel-plate capacitor 161. The signals may be electrical signals for which a voltage, current, impedance, capacitance, or inductance varies based on a level of the PPOI.

At 206, the signals are converted to physiologic data indicative of the PPOI via one or more processors 155 of the sensor 150. The one or more processors 155 may convert the signals generated by the sensing circuit 152 to the physiologic data by digitizing the signals to form the physiologic data. At 208, the physiologic data is stored in a memory 160 of the sensor 150, at least temporarily. The memory 160 may store the physiologic data until the one or more processors 155 direct a communications circuit 158 to transmit the physiologic data.

At 210, the communications circuit 158 of the sensor 150 is directed to transmit the physiologic data to an implantable medical device (IMD) 100 and/or an external device (ED) 104. The communications circuit 158 may be directed (e.g., via the one or more processors 155) to retrieve the physiologic data from the memory 160 and transmit the physiologic data to another device. The transmission may be performed in response to receiving a request by the IMD 100 and/or the ED 104. Furthermore, the communications circuit 158 may be prompted to transmit the physiologic data in response to an internal clock 153 indicating that it is time to transmit the physiologic data according to a predetermined schedule that is stored in the memory 160.

At 212, a determination is made whether the physiologic data that is transmitted indicates a change that prompts a modification of treatment provided by the IMD 100 to the patient. The change may be a PPOI value that falls outside of a designated range, such as above or below respective thresholds. If the determination is in the affirmative, then flow proceeds to 214 and at least one parameter of the therapy provided by the IMD 100 is modified based on the physiologic data received from the communications circuit 158 of the implantable sensor 150. If there is no change or the change is minor and within the designated range, then the determination at 212 is in the negative and flow proceeds to 216 in which the current treatment provided by the IMD 100 to the patient is maintained.

Figure 7:
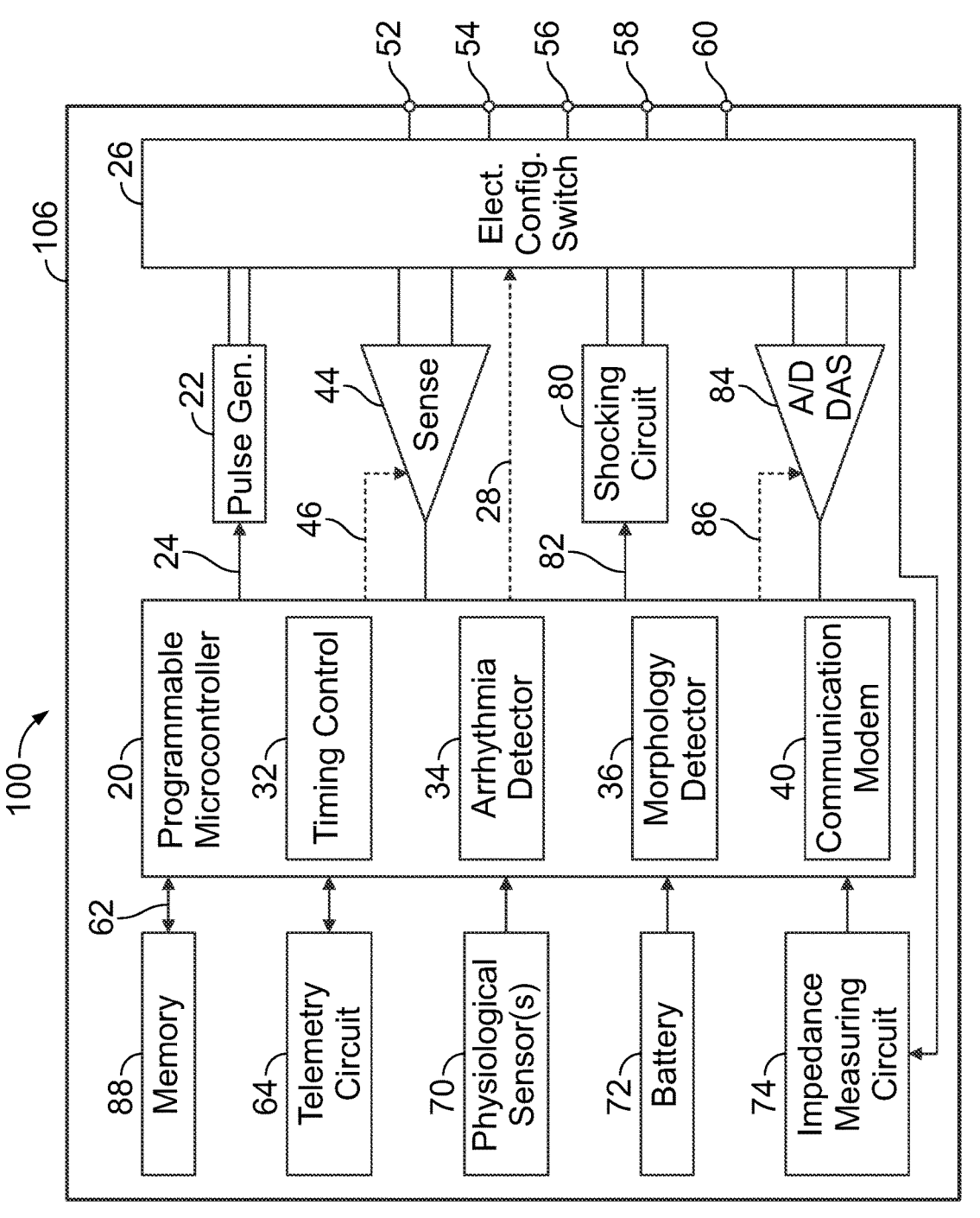
FIG. 7 shows a block diagram of the IMD according to an embodiment.

FIG. 7 shows a block diagram of the IMD 100 according to an embodiment. The IMD 100 shown in FIGS. 1 and 2 is not limited to the features described in this embodiment. The housing 106 or case of the IMD 100 holds the electronic and/or computing components. The housing 106 further includes a connector (not shown) with at least one terminal 52 and optionally additional terminals 54, 56, 58, 60. The terminals may be connected to electrodes that are located in various locations within and about the heart, such as on the electrodes 122, 123, 132, 134, 136, 138 on the leads 120, 130 (shown in FIG. 1). The electrodes may include various combinations of ring, tip, coil, shocking electrodes, and the like.

The IMD 100 includes a programmable microcontroller 20 that controls various operations of the IMD 100, including cardiac monitoring and stimulation therapy. Microcontroller 20 includes a one or more processors (e.g., a micro-processors or equivalent control circuitry), RAM and/or ROM memory, logic and timing circuitry, state machine circuitry, and I/O circuitry. Microcontroller 20 includes an arrhythmia detector 34 that is configured to cardiac activity data to identify potential atrial fibrillation (AF) episodes as well as other arrhythmias (e.g., tachycardias, bradycardias, asystole, etc.).

An electrode configuration switch 26 is optionally pro-vided to allow selection of different electrode configurations under the control of the microcontroller 20. The electrode configuration switch 26 may include multiple switches for connecting the desired electrodes to the appropriate I/O circuits, thereby facilitating electrode programmability. The switch 26 is controlled by a control signal 28 from the microcontroller 20. Optionally, the switch 26 may be omit-ted and the I/O circuits directly connected to a housing electrode.

The IMD 100 may include a chamber pulse generator 22 that generates stimulation pulses for connecting the desired electrodes to the appropriate I/O circuits, thereby facilitating electrode programmability. The pulse generator 22 is con-trolled by the microcontroller 20 via control signals 24. The IMD 100 includes a sensing circuit 44 selectively coupled to one or more electrodes that perform sensing operations through the switch 26 to detect cardiac activity. The sensing circuit 44 may include dedicated sense amplifiers, multi-plexed amplifiers, or shared amplifiers. The sensing circuit 44 may operate in a unipolar sensing configuration or a bipolar sensing configuration. The output of the sensing circuit 44 is connected to the microcontroller 20 which, in turn, triggers, or inhibits the pulse generator 22 in response to the absence or presence of cardiac activity. The sensing circuit 44 receives a control signal 46 from the microcon-troller 20 for purposes of controlling the gain, threshold, polarization, and timing of any blocking circuitry (not shown) coupled to the sensing circuit.

The IMD 100 further includes an analog-to-digital A/D data acquisition system (DAS) 84 coupled to one or more electrodes via the switch 26 to sample cardiac signals across any pair of desired electrodes. The A/D DAS 84 is controlled by a control signal 86 from the microcontroller 20.

The IMD 100 is further equipped with a communication modem (modulator/demodulator) or circuit 40 to enable wireless communication. The communication circuit 40 enables timely and accurate data transfer directly between the IMD 100 and the sensor 150 and/or between the IMD 100 and the external device 104. In an embodiment, the communication circuit 40 receives physiologic data, repre-sentative of a PPOI, that is generated and communicated by the implantable sensor 150. The communication circuit 40 conveys the physiologic data to the microcontroller 20 for analysis and potentially updating one or more treatment settings or parameters provided by the IMD 100 to the patient based on the newly received physiologic data. The wireless communication link with the external device 104 also enables the IMD 100 to communicate the physiologic data, or a message based on the physiologic data, to one or more external devices to facilitate access by physicians and/or patients to the data generated by the sensor 150.

The communication circuit 40 may utilize radio frequency (RF), Bluetooth, or Bluetooth Low Energy telemetry proto-cols. The signals are transmitted in a high frequency range and will travel through the body tissue in fluids without stimulating the heart or being felt by the patient. The communication circuit 40 may be implemented in hardware as part of the microcontroller 20, or as software/firmware instructions programmed into and executed by the micro-controller 20. Alternatively, the circuit 40 may reside sepa-rately from the microcontroller 20 as a standalone hardware component.

The microcontroller 20 is coupled to a non-transitory data storage device, referred to herein as memory device 88, by a suitable data/address bus 62. The memory device 88 stores programmable operating parameters used by the microcon-troller 20 and/or data associated with the detection and determination of arrhythmias.

The IMD 100 optionally includes one or more physiologic sensors 70 that are utilized by the microcontroller 20 to adjust treatment settings or parameters. The physiologic sensors 70 may sense changes in pacing stimulation rates, changes in cardiac output, changes in the physiological condition of the heart, and/or diurnal changes in activity (e.g., detecting sleep and wake states). Examples of physi-ological sensors 70 might include sensors that, for example, sense respiration rate, pH of blood, ventricular gradient, activity, body movement, position/posture, minute ventila-tion (MV), and/or the like.

The battery 72 provides operating power to all of the components in the IMD 100. The battery 72 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more).

The IMD 100 further includes an impedance measuring circuit 74, which can be used for many things, including sensing respiration phase. The IMD 100 may be further equipped with a telemetry circuit 64 that can selectively communicate with an external device, such as the device 104, when connected via a physical (e.g., wired) communi-cation link. The IMD 100 includes a shocking circuit 80 controlled by control signals 82 generated by the microcon-troller 20. The shocking circuit 80 generates shocking pulses of low (e.g., up to 0.5 joules), moderate (e.g., 0.5-10 joules), or high energy (e.g., 11 to 40 joules), as controlled by the microcontroller 20. In an alternative embodiment in which the IMD 100 senses and monitors cardiac activity without administering stimulation therapy, the IMD 100 may lack the pulse generator 22 and the shocking circuit 80.

The microcontroller 20 may include other dedicated cir-cuitry and/or firmware/software components, such as a tim-ing control (module) 32 and a morphology detector (mod-ule) 36. The timing control 32 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection win-dows, evoked response windows, alert intervals, marker channel timing, and the like. The morphology detector 36 is configured to review and analyze one or more features of the morphology of cardiac activity signals, such as the mor-phology of detected R waves to determine whether to include or exclude one or more beats from further analysis.

The embodiments described herein provide an implant-able medical sensor that has a small form factor designed to enable the sensor to be implanted within small volumes, such as within a blood vessel. The sensor includes an onboard power source that powers the generation and trans-mission of physiologic data representative of a PPOI. The physiologic data is transmitted from the sensor to another device, which may be another implanted device within the same patient (e.g., an IMD). The sensor is able to accomplish such operation with a power source that fits within the small form factor by using various power-conservation techniques. For example, the sensor may function in a low-power sleep mode most of the time except when prompted, via a clock according to a schedule or via a received request, to wake in order to collect and/or transmit additional physiologic data. Furthermore, the sensor may utilize an IMD as a communication bridge or relay to avoid consuming energy on transmitting the physiologic data directly from the sensor to an external device. In addition, the power source of the sensor may be rechargeable, such that the power source can charge when implanted, to prolong the operational lifespan of the sensor within the patient. A technical benefit of the implantable medical sensor is the lack of reliance on patient involvement to collect the physiologic data. The sensor may autonomously operate, which can provide more reliable and consistent real-time data updates than relying on active participation of the patient. The sensor may provide real-time on-demand updates upon request. The reliable, consistent data updates and on-demand updates can improve the patient outcome by enabling more timely treatment modifications based on measured changes in physiologic condition of the patient.

In an embodiment, a method for collecting real-time on-demand measurements includes assembling an implantable sensor to include a power source, a sensing circuit, a communications circuit, a memory, and one or more processors. The sensing circuit is configured to sense a physiologic parameter of interest (PPOI) and to generate signals indicative of the PPOI. The communications circuit is configured to communicate with at least one of an implantable medical device (IMD) or an external device (ED). The memory is configured to store program instructions, and the one or more processors are coupled to the memory. The method also includes collecting, via the one or more processors executing the program instructions, real-time on-demand measurements. The measurements are collected by activating the sensing circuit to generate the signals indicative of the PPOI, converting the signals to physiologic data indicative of the PPOI, storing the physiologic data in the memory, and directing the communications circuit to transmit the physiologic data to the at least one of the IMD or the ED.

The method may include receiving a data collection instruction, and performing the activating, converting, storing and directing operations in response to the data collection instruction in real-time on-demand.

The method may include storing a data collection schedule in the memory, and performing the activating, converting, and storing operations based on the data collection schedule in real-time.

The method may include storing the physiologic data over a collection period of time, and performing the directing operation to transmit the physiologic data in real-time at least one of i) on-demand upon request from at least one of the IMD or the ED, or ii) at a time according to a predetermined data transmission schedule.

The method may include delivering a therapy, via an IMD, and modifying at least one parameter of the therapy in response to receiving and analyzing the physiologic data from the implantable sensor.

The method may include communicating bidirectionally with the IMD through at least one of far field radio frequency wireless communication, conductive communication, or a direct wired connection.

The method may include storing, in the power source, an amount of energy to supply the sensing circuit, the communications circuit, and the one or more processors for at least a predetermined number of data collection operations and communication sessions, and performing the data collection operations and communication sessions without any external energy delivery.

The method may include assembling the sensor to include a housing having a hermetically sealed interior cavity that holds the sensing circuit, the memory, the one or more processors, and the communications circuit, including a radiofrequency (RF) antenna of the communications circuit. The housing at least partially composed of a resistive material at least partially transparent to RF fields. Optionally, the RF antenna is at least one of i) a surface mount chip antenna, or ii) a conductive metallic trace arranged in a serpentine design. The assembling operation may include locating the RF antenna on a printed circuit board or on an inner wall of the housing.

The method may include assembling the sensor to include a first housing portion at a first end of the sensor, a second housing portion at a second end of the sensor opposite the first end, and a flexible cable disposed between and connected to the first and second housing portions. The assembling operation may include installing a first electrode of the communications circuit to the first housing portion and a second electrode of the communications circuit to the second housing portion. The sensor is assembled to electrically couple the first electrode to the second electrode via the flexible cable. The directing operation includes directing the communications circuit to transmit the physiologic data by applying voltage bursts to the first and second electrodes to create a polarized electric field around the sensor.

The method may include retaining the one or more processors in a sleep mode until transitioning the one or more processors to a wake mode responsive to receiving a wake-up instruction from a clock of the implantable sensor. At least one of the activating, converting, storing, and directing operations are performed when in the wake mode. Optionally, the method includes supplying power to the clock without supplying power to (any of) the one or more processors, the sensing circuit, and/or the communications circuit, when the one or more processors are in the sleep mode.

The sensing operation may include sensing, as the PPOI, at least one of pressure, temperature, respiration, or a body generated analyte (BGA). The signals generated by the sensing circuit represent electrical signals, for which at least one of voltage, current, capacitance, inductance or resistance varies based on a level of the PPOI.

The method may include electrically connecting a secondary battery, which represents the power source, to one of (i) the IMD via a direct wired connection to receive electrical power from the IMD or (ii) an energy harvesting unit of the sensor. The energy harvesting unit includes a coil configured to inductively connect to an external recharge device to transfer electrical power from the external recharge device to the secondary battery via the energy harvesting unit In accordance with embodiments herein, the methods, devices, and systems may be implemented in connection with the holistic systems and methods described in U.S. patent application Ser. No. 16/930,791, filed on Jul. 16, 2020 and entitled Methods, Devices and Systems for Holistic Integrated Healthcare Patient management, which is incorporated herein by reference in its entirety.

Figures 8, 9A:
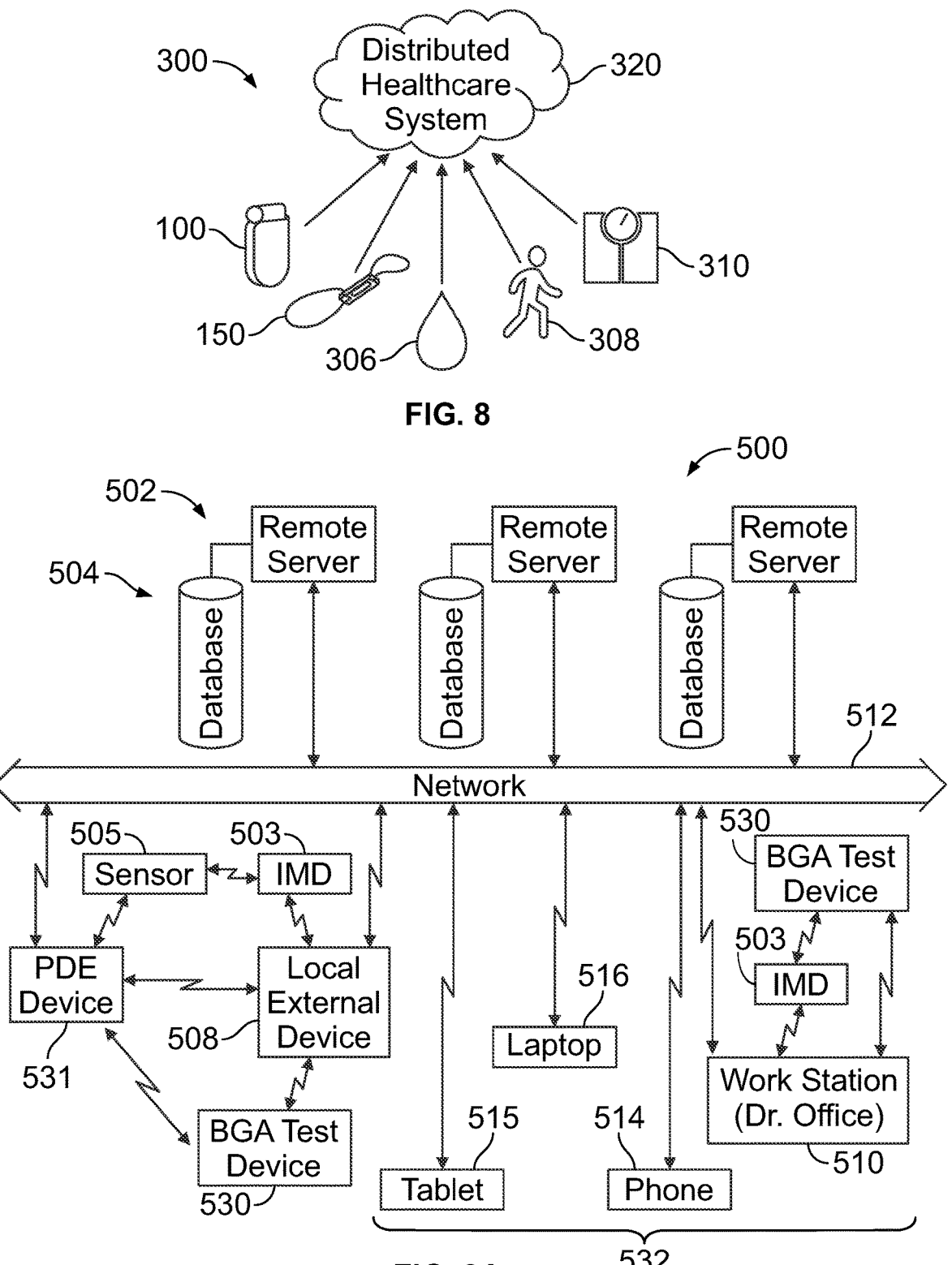
FIG. 8 illustrates a block diagram of a system for integrating external diagnostics with remote monitoring provided by implantable medical devices in accordance with embodiments herein.
FIG. 9A illustrates a healthcare system formed in accordance with embodiments herein.

FIG. 8 illustrates a block diagram of a system 300 for integrating external diagnostics with remote monitoring of data generated by implantable medical devices in accordance with embodiments herein. The system 300 may be implemented with various architectures that are collectively referred to as a distributed healthcare system 320. The healthcare system 320 may be implemented with the implantable sensor 150 described according to the embodiments herein. The healthcare system 320 is configured to receive data from a variety of external and implantable sources including, but not limited to, active IMDs 100 capable of delivering therapy to a patient, the implantable sensor 150, BGA test devices 306, wearable sensors 308, and point-of-care (POC) devices 310 (e.g., at home or at a medical facility). Optionally, a POC device 310 may represent one type of BGA test device 306.

The data from one or more of the external and/or implantable sources is collected and transmitted to one or more secure databases within the healthcare system 320. Optionally, the patient and/or other users may utilize a patient data entry (PDE) device, such as a smart phone, tablet device, etc., to enter behavior related medical (BRM) data. For example, a patient may use a smart phone to provide feedback concerning activities performed by the patient, a patient diet, nutritional supplements and/or medications taken by the patient, how a patient is feeling (e.g., tired, dizzy, weak, good), etc.

For example, the external BGA test device 306 may collect lab test results for specific tests and then transmit the lab test results to the healthcare system 320. The BGA test device 306 may measure and/or sense one or more body generated analytes (e.g., blood glucose). For example, a cartridge based BGA test device may be configured to test patient levels for one or more body generated analytes. The BGA test device 306 may be implemented at a variety of physical locations, such as one or more "core" laboratories, a physician's office, ER (emergency room), OR (operating room) and/or a medical facility POC (e.g., during hospitalizations or routine healthcare visits). Optionally, the BGA test device 306 may be implemented as a fully implantable "lab on a chip", such as an implantable biosensor array, that is configured to collect lab test results.

The at-home POC device 310 may periodically or continuously monitor the body generated analytes (e.g., blood glucose) measured by the BGA test device 306. The at-home POC device 310 may transmit the raw BGA data to the medical network (e.g., a local external device and/or remote server). Additionally or alternatively, the at-home POC device 310 may analyze the BGA data and/or perform a test of the BGA data for a characteristic of interest (COI) such as a malnutrition state COI, an electrolyte COI, a cardiac marker COI, a hematology COI, a blood gas COI, a coagulation COI, an endocrinology COI. The POC device 310 transmits the COI (and optionally the BGA data) to the healthcare system 320 as the tests are performed at home or elsewhere. The POC device 310 may implement periodic or continuous tests for glucose levels, such as through sensors and handheld devices offered under the trademark FREE-STYLE LIBRE® by Abbott Laboratories.

In an embodiment, the components of the system 300 may be independently powered and capable of communicating with each other. For example, the sensor 150 can communicate physiologic data to the IMD 100, the BGA test device 306, the wearable sensor 308, and/or the POC devices 310. Measurements by the sensor 150 may be synchronized with measurements by the IMD 100, the BGA test device 306, and/or the wearable sensor 308. The synchronized measurements may be transmitted to a common device, such as a POC device 310 or a PDE device, to enable real-time, on-demand analysis of multiple different physiologic conditions in combination. For example, up-to-date blood glucose data may be analyzed with up-to-date blood pressure data from the sensor 150 to enable more timely treatment modifications based on measured changes in physiologic condition of the patient.

In an embodiment, the device that analyzes the data may calculate a health risk index based on the incoming BGA data, sensor physiologic data, and/or IMD data, alone or in combination with previously stored data. The health risk index represents a general indicator of a degree to which the patient is experiencing a health state or potential health risk. As a patient's health deteriorates, indicated by one or more characteristics reflected in the BGA, sensor, and IMD data, the health risk index will similarly elevate. When the health risk index is determined by the device (e.g., the POC device 310, a PDE device, the IMD 100, etc.) to exceed a designated threshold, the device determines that the patient's health condition is deteriorating and intervention is appropriate. The device may generate a treatment notification based on the treatment diagnosis, and directs the treatment notification to be sent to the patient and/or a care provider. The treatment notification may include an instruction or recommendation to modify treatment of the patient. The treatment modification may include changing a cardiac stimulation therapy delivered by the IMD. The device may also instruct the BGA test device 306, the sensor 150, and the IMD 100 to collect supplemental data for confirming the diagnosis and tracking the condition of the patient.

For example, the IMD 100 may track the IMD data and detect possible deterioration of a patient's health. When the IMD 100 detects possible deterioration, the IMD notifies the implantable sensor 150 to perform a measurement to collect supplemental physiologic data indicative of the PPOI. Optionally, when the IMD detects possible deterioration, the IMD may also automatically convey a device command (as a treatment notification) to the BGA test device 306. In response, the BGA test device 306 may automatically collect supplemental BGA data. This combination of IMD data, sensor physiologic data, and BGA data, collected in real-time on-demand without patient intervention, is analyzed to diagnose and modify treatment of the patient.

FIG. 9A illustrates a healthcare system 500 formed in accordance with embodiments herein. The healthcare system 500 includes one or more remote servers 502, each of which is connected to one or more database 504. The servers 502 and databases 504 may be located at a common physical location and/or distributed between multiple remote locations within a city, state, country or worldwide. The servers 502 communicate with at least one network 512. The network 512 may be the internet, a voice over IP (VoIP) gateway, a local plain old telephone service (POTS) such as a public switched telephone network (PSTN), a cellular phone-based network, and the like. Alternatively, the network 512 may be a local area network (LAN), a campus area network (CAN), a metropolitan area network (MAN), or a wide area network (WAM). The network 512 facilitates the transfer/receipt of information such as IMD data, sensor physiologic data, and BGA data.

The system 500 also includes one or more IMDs 503, one or more implantable medical sensors 505, one or more local external devices 508, one or more BGA test devices 530, one or more PDE devices 531, and one or more medical personnel (MP) devices 532, all of which communicate (directly or indirectly) through the network 512 to the servers 502 and/or one another. The servers and devices described herein may wirelessly communicate with one another utilizing various protocols, such as Bluetooth, GSM, infrared wireless LANs, HIPERLAN, 3G, satellite, as well as circuit and packet data protocols, and the like. Alternatively, a hard-wired connection may be used to connect the servers and devices.

The IMD 503 may be the IMD 100 described in embodiments herein. The sensor 505 may be the sensor 150 described in embodiments herein. The IMD 503 may collect various types of data, such as cardiac electrical and/or mechanical activity data, PAP or other pressure related data, impedance data, RPM data, flow data, and the like. The sensor 505 may measure a PPOI, such as blood pressure, temperature, respiration, capacitance, resistance, etc. The BGA test device 530 may analyze various types of body generated analytes to derive the BGA data. The PDE device 531 collects BRM data, such as based on manual inputs from a patient or other user, and/or based on automatic video and/or audio monitoring.

The local external device 508 may be implemented as a variety of devices including, but not limited to, medical personnel programmer, a local RF transceiver and a user workstation, smart phone, tablet device, laptop computer, desktop computer and the like. The MP devices 532 may also be implemented as a variety of devices including, but not limited to, medical personnel programmer, workstation, smart phone, tablet device, laptop computer, desktop computer and the like. Functionality of the MP devices 532 related to embodiments herein may be implemented through dedicated hardware circuits, firmware, software, and/or application operating on one or more computing devices. The MP devices 532 may include a cell phone 514, a tablet device 515, a laptop 516, and/or the like.

The server 502 is a computer system that provides services to other computing systems over a computer network. The servers 502 control the communication of information including IMD data, sensor physiologic data, patient entered data, medical record information and BGA. The servers 502 interface with the network 512 to transfer information between the servers 502, databases 504, local external devices 508, PDE device 531, medical personnel devices 532 for storage, retrieval, data collection, data analysis, diagnosis, treatment recommendations and the like. The databases 504 store all or various portions of the information described herein, including, but not limited to, IMD data, sensor physiologic data, BGA data, BRM data, medical record information, treatment diagnoses and recommendations, and the like.

The local external device 508 may reside in a patient's home, a hospital, or a physician's office. The local external device 508 communicates wired or wirelessly with the IMDs 503, the sensors 505, and/or BGA test devices 530. The local external device 508, when implemented as a programmer, may be configured to acquire cardiac signals from the surface of a person (e.g., ECGs), and/or intra-cardiac electrogram (e.g., IEGM) signals from the IMD 503. The local external device 508 interfaces with the network 512 to upload the data and other information to the server 502. The workstation 510 may interface with the network 512 to download various data, information, diagnoses and treatment recommendations from the database 504.

The distributed "digital" healthcare system collects various types of data, enables the data to be analyzed by various computing devices within the system, and determines one or more treatment diagnosis and treatment recommendation substantially in real-time with the collection of new data. In this manner, unneeded and undesired hospitalizations may be avoided through preventative detection, reducing costs associated with emergency medical procedures. Additionally, such a system also assists in prolonging a human's life and increases patient care. Thus, an improved system and methodology are provided.

Figure 9B:
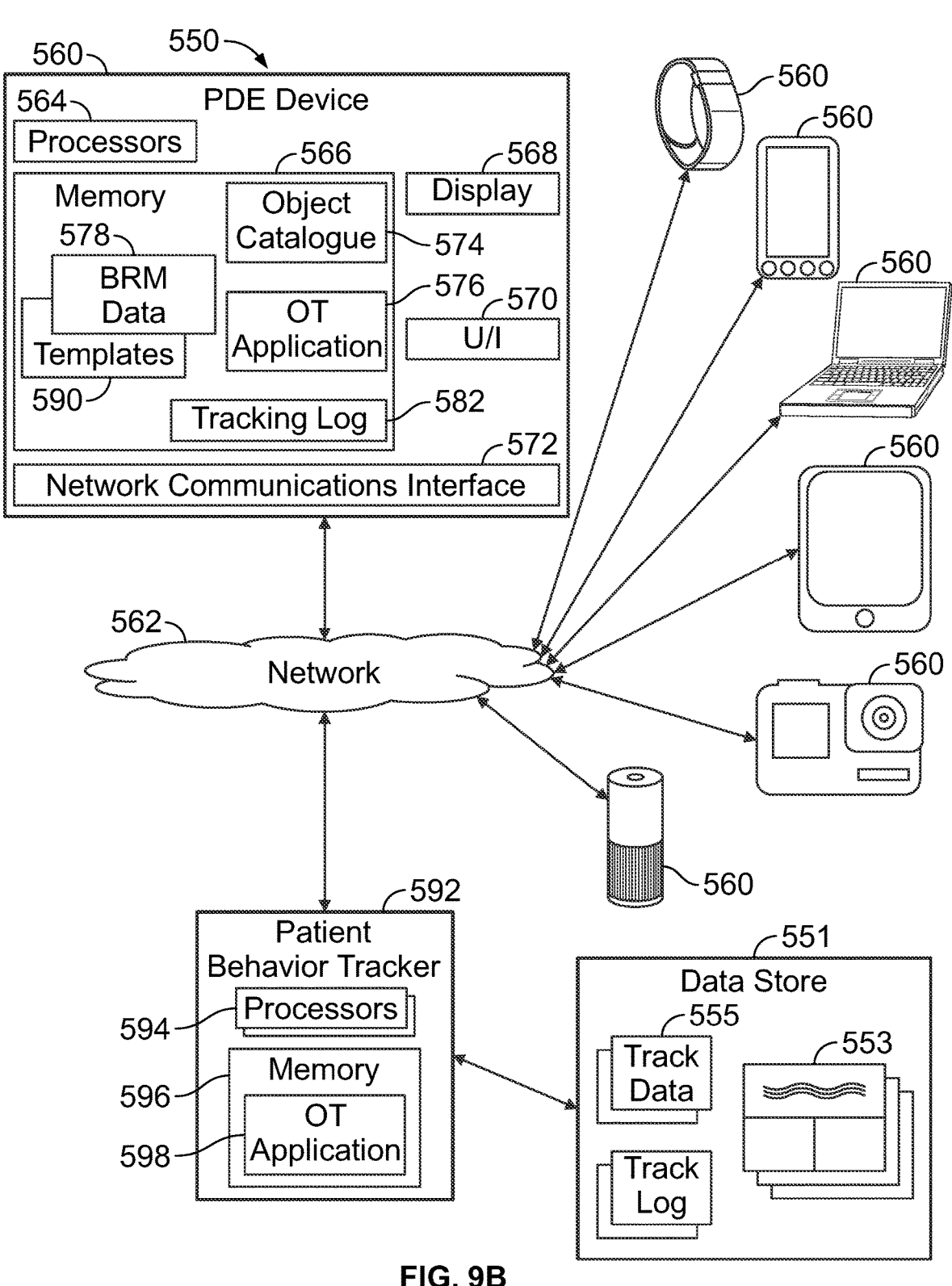
FIG. 9B illustrates a distributed healthcare system that collects and analyzes patient data in accordance with embodiments herein.

FIG. 9B illustrates a distributed healthcare system 550 that collects and analyzes patient data in accordance with embodiments herein. The system 550 includes one or more patient data entry (PDE) devices 560 that communicate over a network 562 with various other devices, such as IMDs, BGA test devices, implantable medical sensors, MP devices, local external devices, servers and the like. When the PDE device 560 includes a GUI, the patient or other user may input patient data in addition to IMD data, sensor data, and BGA data. The PDE devices 560 may include one or more input devices, such as microphones, cameras, buttons, touchpads, and the like. One or more of the PDE devices 560 may include one or more processors 564, memory 566, a display 568, a user interface 570, a network communications interface 572, and various other mechanical components, electrical circuits, hardware and software to support operation of the PDE device 560. Optionally, the PDE device 560 may include an atmospheric pressure gauge that monitors atmospheric pressure either periodically or on-demand. The on-demand or time-stamped atmospheric pressure measurement of PDE 560 can be used to convert time-stamped or time-synchronized absolute blood pressure measured by the sensor 150 to relative blood pressure, upon time-synchronization of the data between the sensor 150 and the PDE 560.

The user interface 570 is configured to receive behavior related medical (BRM) data related to information indicative of an action or conduct by a patient that will affect one or more physiologic characteristics of interest and/or information indicative of a present state experienced by a patient in connection with a physiologic characteristic of interest. The user interface 570 may include a variety of visual, audio, and/or mechanical devices, such as the input devices listed above. The user interface 570 can include a visual, mechanical, and/or audial output device. The user interface 570 permits the user to enter or generate the BRM data. As nonlimiting examples, the patient or a third-party (e.g., family member, caregiver) may enter, through the PDE device 560, information related to the patient's diet and/or nutritional supplements (e.g., what, when and how much a patient is taking), information concerning whether a patient is following a physician's instructions, information indicative of a present state experienced by the patient and the like. For example, a user may use a keyboard, touch screen and/or mouse to enter BRM data. Optionally, the user may enter the BRM data through spoken words (e.g., "Alexa I just took my medication", "Alexa I am eating 3 slices of peperoni pizza", "Alexa I am eating an apple", "Alexa I am drinking a 12 oz. soda and eating a candy bar).

Optionally, the PDE device may automatically monitor actions or conduct of interest. For example, the PDE device may include a position tracking device sold under the trademark FITBIT® by Fitbit Inc. or other types of position tracking devices. The position tracking device may monitor and collect, as BRM data, movement information, such as a number of steps or distance traveled in a select period of time, a rate of speed, a level of exercise and the like. Optionally, the PDE device may monitor and collect, as BRM data, heart rate.

The memory 566 can encompass one or more memory devices of any of a variety of forms (e.g., read only memory, random access memory, static random access memory, dynamic random access memory, etc.) and can be used by the processor 564 to store and retrieve data. The data that is stored by the memory 566 can include, but need not be limited to, operating systems, applications, and other information, in addition to BRM data 578.

The network communications interface 572 provides a direct connection to other devices, auxiliary components, or accessories for additional or enhanced functionality, and in particular, can include a USB port for linking to a user device with a USB cable. Optionally, the network communications interface 572 may include one or more transceivers that utilize a known wireless technology for communication.

In connection with embodiments that automatically collect BRM data, the memory 566 includes, among other things, an object tracking (OT) application 576, object catalogue 574, BRM data 578, a tracking log 582 and one or more templates 590. The memory 566 may store pick-up zones, drop-off zones, secure zones and access levels as described herein. The functionality of the OT application 576 is described below in more detail. The templates 590 may include one or more types of templates that are descriptive of, and associated with, food objects, nutritional supplement objects, and other objects of interest.

The BRM data 578 may be collected over the network 562 from numerous types of PDE devices 560 that implement a tracking operation (also referred to as tracking devices). For example, different types of electronic tracking devices 560 may collect image-based tracking data, audio-based tracking data, voice-based tracking data and gesture-based tracking data. The OT application 576 utilizes the templates 590 to analyze incoming data to identify objects of interest. The OT application 576 updates the tracking log 582 based on the analysis.

In the foregoing example, the PDE device 560 implements the OT application 576 locally on a device that may be generally present within the physical area of a user. For example, the PDE device 560 may represent the user's cell phone, laptop computer, tablet device, DPA device and the like.

Additionally or alternatively, all or portions of the OT application may be implemented remotely on a remote resource, referred to as a patient behavior tracker 592. The patient behavior tracker 592 includes one or more processors 594 that may perform limited operations, such as manage storage and creation of templates. The patient behavior tracker 592 may provide access to one or more memory 596, and/or implement the OT application 598. The patient behavior tracker 592 communicates with PDE devices 560 through one or more networks 562 to provide access to object catalogs and to implement processes described herein. The patient behavior tracker 592 may represent a server or other network-based computing environment. The patient behavior tracker may represent a single computing device, or a collection of computer systems located at a common location or geographically distributed.

The patient behavior tracker 592 includes one or more processors 594 and memory 596, among other structures that support operation thereof. In accordance with embodiments herein, the patient behavior tracker 592 receives requests from various PDE devices 560 and returns resources in connection there with.

The memory 551 of the data store may store the object catalogs 553 organized in various manners and related to a wide variety of objects and types of tracking data. The object catalogs 553 may include various types of templates corresponding to different types of objects. Optionally, the memory 551 may store BRM data 555, along with timing information such as when the patient behavior tracker 592 receives the BRM data 555 from PDE devices 560 that are performing tracking operations.

In an embodiment, the patient behavior tracker 592 and/or the PDE devices 560 may communicate with implanted medical devices, such as the implantable sensor 150 and the IMD 100. Operations of the sensor 150 and/or the IMD 100 may be responsive to operations performed by the patient behavior tracker 592 and/or the PDE devices 560, and vice-versa. For example, BRM data 578 generated by a PDE device 560 may indicate that the patient has a certain designated posture. The PDE device 560 may communicate with the IMD 100, via the network 562, to inform the IMD 100 that the patient has the designated posture. In response to receiving the notification, the IMD 100 may take one or more actions, such as generating supplemental IMD data of the patient by measuring physiologic conditions, communicating the notification to the sensor 150, and/or initiating or modifying stimulation therapy provided by the IMD 100. The IMD 100 may forward the notification to the sensor 150 as a command to generate supplemental sensor physiologic data and communicate the supplemental sensor data to the IMD 100. As described, a single sensed event (e.g., a posture, detecting a physiologic data value or trend outside of a designated range, a user input, etc.) external to a patient can trigger the implanted sensor 150 and/or another medical device to take action without human intervention. The automated responses can provide updated information about multiple different parameters of a patient condition in real-time and on-demand to provide a greater indication of overall patient condition than a single patient parameter can.

The following example explains how BRM data and/or BGA data can be used to automatically trigger the collection of physiologic data by the implantable sensor 150. The BGA test device and/or PDE device may track BGA and/or BRM data and detect possible deterioration of patient health. For example, the BGA data trend may cross a threshold, change direction or increase a downward trend. When the BGA test device detects possible deterioration, the BGA test device may automatically convey a device command (as a treatment notification) to the IMD 100 and/or the sensor 150 to collect supplemental sensor physiologic data. In response to receiving the command, the sensor 150 automatically collects physiologic data. Additionally or alternatively, a PDE device may analyze BRM data to identify when a BRM data trend crosses a threshold, changes direction, or increases a downward trend. The PDE device may identify an extended period of time in which no new BRM data is entered (e.g., an indicator of transmission noncompliance). When the PDE device detects possible deterioration and/or noncompliance, the PDE device may automatically convey a device command (as a treatment notification) to the IMD 100 and/or the sensor 150 to collect supplemental sensor physiologic data. In accordance with at least some embodiments, the various sources of information allow for remote monitoring to enable decision-making without any active input from the patient.

The supplemental sensor physiologic data is then conveyed to a processing device for analysis. For example, the sensor 150 may communicate the sensor data to the IMD 100, which may process the data and/or may forward the sensor data to an external device (e.g., the external device 104) for processing. The processing device calculates an IMD-based index (IMD Index) based on the new sensor physiologic data and/or IMD data generated by the IMD. Examples are discussed below for different physiologic COI that may be monitored in connection with different types of IMD Index calculations. For example, an IMD Index may represent a PAP systolic level, PAP diastolic level, PAP mean and the like. As another example, the IMD Index may represent a diuretic response profile that is calculated based on hemodynamic data (from the sensor data) and diuretic medication information. As another example, the IMD Index may represent PAP levels and/or trends derived from the sensor data. As another example, the IMD Index may represent ST segment levels and/or ST segment level shifts determined from cardiac activity data within IMD data generated by the IMD. As another example, the IMD Index may represent levels and/or trends in cardiac output, thoracic impedance, cardiogenic impedance, heart sounds and the like. As another example, the IMD Index may represent AF burden calculated based on CA signals indicative of AF episodes. The IMD Index may further represent MCS parameter levels and/or trends. Optionally, the processor may classify the IMD Index based on various predetermined criteria.

The processing device may receive data from multiple different sources/modalities. In order to organize and synchronize the data, the processing device may correlate a time stamp associated with the receipt of each collection of data, including IMD data, sensor physiologic data, BRM data, and/or BGA data. The processing device may analyze the sensor data, the IMD data, BRM data and BGA data in connection with one or more application specific models (ASM) to generate a treatment diagnosis and calculate a health risk index related to the treatment diagnosis. The ASM may be implemented in various manners, including but not limited to threshold-based algorithms, template correlation algorithms, lookup tables, decision trees, machine learning algorithms and the like. The ASM analyzes data points from dissimilar data sources (e.g., from the IMD, sensor, BRM and BGA data) relative to one another to generate the treatment diagnosis. The data points from the IMD, sensor, BRM and BGA data have a relative level of importance with respect to one another, that varies, in connection with calculating the health risk index and generating the treatment diagnosis. The relative level of importance may vary in the context of a particular disease state or health risk index of interest.

The processing device identifies a treatment diagnosis and treatment notification to be provided in connection with the health risk index. Treatment diagnoses and recommendations may relate to changes in prescriptions, changes in parameters of an IMD and the like. Additionally, treatment diagnoses and recommendations may be implemented in connection with digital health/patient application features that are communicated to the patient through smart phone or another electronic device. For example, an application implemented on a smart phone may allow a patient to track calorie, salt and fat intake as BRM data.

As one example, updated sensor physiologic data (from the implantable sensor 150) may indicate that a patient's PAP level has increased (relative to prior PAP data). If the PAP levels were considered alone, a potential or candidate treatment diagnosis and recommendation would be to change the patient's diuretic medication (e.g., increase the dosage or change the type of diuretic if the patient is exhibiting a resistance to a particular diuretic). However, in the present example, BGA data is also obtained and analyzed contemporaneous in time with the sensor data. The BGA data may indicate that a blood glucose level is high, and a patient's diabetes may be in an uncontrolled state. The ASM analyzes the blood glucose level information in combination with the PAP information. Given the increase in the blood glucose level, the ASM may determine that it is not preferable to change the diuretic prescription at this time. Instead, the ASM generates a diagnosis and treatment recommendation that first treats the blood glucose level. Once the blood glucose level has returned to an acceptable range, the ASM may then render the diagnosis and treatment recommendation that treats the elevated PAP level. In the present example, the ASM affords a lower weight (or degree of importance) to the elevated PAP level in the decision-making process, given that the patient was also experiencing an unduly high blood glucose level.

By way of example, prior to rendering a diagnosis and treatment recommendation, the ASM may determine that additional information is warranted. For example, the ASM may determine that updates or re-measurements of one or more sensor physiologic parameters and/or BGA parameters is warranted. In the event that additional sensor and/or IMD data is needed, the ASM may convey a device command to the IMD to obtain and return the additional desired sensor and/or IMD data. Additionally or alternatively, the ASM may desire additional BGA data. Once the additional information is collected, the ASM may complete the analysis of the original and additional IMD, sensor, BGA and/or BRM data. In the event that the PAP level remains elevated, the ASM may render a diagnosis and treatment recommendation to treat the elevated PAP level. In the example above, the operations of the ASM may be performed by a processing device that implements the ASM.

In another example, embodiments may "override" an otherwise permanent change in a therapy/prescription based on elevated activity. For example, a patient may exhibit a level of activity that is unusually high relative to a preprogrammed activity level and/or a patient's history of activity. When the patient exhibits an unusually high level of activity for a select period of time, the ASM may recognize such behavior and determined that changes in the IMD data, BGA data and/or BRM data may not be indicative of a degradation of the health risk index and thus may not warrant a change in therapy/prescription. For example, when the patient undergoes an unusually high level of activity for an extended period of time during exercise, the patient's blood pressure may become unusually elevated, but does not warrant a therapy/prescription change. Additionally or alternatively, when a patient exhibits an unduly high level activity for a select period of time, the ASM may determine that the patient is not prescription compliant (e.g., the patient is not maintaining within a prescribed activity range), and thus may convey a communication to the patient recommending that the patient reduce the activity level.

When a patient with an IMD and/or BGA test device (who is diabetic or otherwise sensitive to sugar) consumes too much sugar, a notification may be sent to the patient to inform that the excessive sugar has caused a spike in the patient's glucose level. As another example, when a patient with an IMD and/or BGA test device avoids exercise for a period of time, the notification may inform a patient that the patient's lack of exercise has raised a PAP trend and/or introduced an undue burden on a patient's kidneys.

The embodiments described herein can be used to identify high risk behavior in heart failure (HF) patients. It has been shown that management of NYHA Class III heart failure based on home transmission of pulmonary artery pressure has significant long-term benefit in lowering hospital admission rates for heart failure. The management of an HF patient is further impacted by the patient's behavioral patterns. For example, aspects of patient behavior that affect progression of HF include, among other things, compliance with medication intake, salt restrictions and activity level and the like.

The sensor data, such as PAP data, may also be beneficial for identifying HF patients who are candidates for implant of a ventricular assist device, a transplant, a valve repair procedure (e.g., a MitraClip™ valve repair to correct mitral regurgitation), and the like.

Embodiments herein describe methods and systems to identify characteristics of the PAP data indicative of poor patient health as well as indicative of candidates for certain types of implants. For example, embodiments herein analyze combinations of cardiac activity signals, such as from an ICM, with PAP data for characteristics indicative of unduly large perfusion resulting from pulmonary hypertension. For example, the ASM may analyze the CA signals and PAP signals in search of certain characteristics of interest in heart rate, arrhythmias pressures and the like. The ICM may measure the heart rate over an extended period of time (e.g. several weeks, months or longer). For example, the ASM may track the level of burden associated with the arrhythmia. Arrhythmias exhibiting high burden (e.g. a large number of events or long duration of events) will exhibit a high PAP pressure. As the PAP pressure reduces, the arrhythmia burden is also reduced. Additionally or alternatively, the active IMD, such as the ICM, may measure activity and provide the activity signals as part of the IMD data. Embodiments herein may examine PAP pressure during exercise to identify a reaction of the level of pulmonary hypertension to the level of exercise. For example, while a patient is exercising, and ICM may measure heart rate, while a PAP sensor measures pressure. As another example, an IMD may utilize an activity sensor to measure a level of exercise, in combination with the PAP sensor measuring pressure. The indication of the level of exercise, in combination with the PAP data, may be analyzed manually or with an ASM in search of an unduly large level of perfusion in connection with pulmonary hypertension.

Embodiments herein may track a manner in which patient behavior modulates PAP daily trends, PAP changes and PAP percentage changes over a week. The implantable sensor 150 is active and automated, which enables the sensor 150 to reliably and consistently provide PAP data, without requiring human intervention, resulting in more timely and accurate data. A higher modulation in PAP over a week is indicative of poorer PAP control which may lead to worsened health and worse outcomes such as hospitalizations. In accordance with aspects herein, methods and systems are provided that allow physicians to titrate a patient's medication based on their behavior and potentially increase the medication dosage on the weekdays with a preponderance of high PA pressures. In accordance with aspects herein, methods and systems are provided that allow patients to modify their behavior to keep spikes in PAP over weekends in check. The patient may be asked to increase/decrease their physical activity or reducing their salt intake based on their weekly PA pressure profiles and thereby managing PAP.

In the embodiments described herein, the various devices trigger corresponding contemporaneous measurements by other devices, on-demand and in real-time, without human intervention. For example, in response to the IMD 100 detecting an increasing AF burden trend, the IMD 100 may command the sensor 150 to perform a contemporaneous PAP measurement. The PAP can be reviewed with the AF in combination to augment treatment and improve diagnosis. In another example, a trend indicating increased BGA, such as due to diet, can be used as the trigger event to command the sensor 150 to perform a PAP measurement. Conversely, a detected increasing PAP trend based on sensor data can be analyzed in conjunction with contemporaneous trends in BGA data, BRM data, and/or cardiac data from the IMD for informed diagnosis.

Terms

The terms "treatment", "arrhythmia treatment", "in connection with treating a heart condition" and similar phrases, as used herein include, but are not limited to, delivering an electrical stimulation or drug therapy to a heart condition. By way of example, treating a heart condition may include, in whole or in part, i) identifying a progression of heart failure over time; ii) confirming an arrhythmia identified by an arrhythmia detection process; iii) instructing the patient to perform a posture recalibration procedure and/or iv) delivering a therapy.

The term "body generated analyte" (BGA) shall mean a test substance or specimen that is naturally generated by or naturally present in a human body. The test substance or specimen may be in liquid form (e.g., blood or other bodily fluid), solid form (e.g., tissue, fat, muscle, bone, or other organ-based material), gas form, cellular form or otherwise. Non-limiting examples of body generated analytes include hematocrit, troponin, CKMB, BNP, beta human chorionic gonadotropin (bHCG), carbon dioxide partial pressure (pCO.sub.2), partial pressure oxygen (pO.sub.2), pH, PT, ACT, activated partial thromboplastin time (APTT), sodium, potassium, chloride, calcium, urea, glucose, creatinine, lactate, oxygen, and carbon dioxide, thyroid stimulating hormone, parathyroid hormone, D-dimer, prostate specific antibody, $TCO_2$, Anion Gap, ionized calcium, urea nitrogen, lactose, hemoglobin, pH, $PCO_2$, $PO_2$, $HCO_3$, Base Excess, $O_2$, ACT Kaolin, ACT Celite, PT/INR, $\beta$-hCG, cTnl, CK-MB, BNP and the like, and combinations thereof. The analyte may be tested in a liquid sample that is whole blood, however other samples can be used including blood, serum, plasma, urine, cerebrospinal fluid, saliva and amended forms thereof. Amendments can include diluents and reagents such as anticoagulants and the like.

The term "BGA test device" shall mean any and all equipment, devices, disposable products utilized to collect and analyze a BGA. The BGA test device may implement one or more of the methods, devices and systems described in the following publications, all of which are incorporated herein by reference in their entireties:

U.S. Pat. No. 8,514,086, entitled "DISPLAYS FOR A MEDICAL DEVICE", issued Aug. 20, 2013;

U.S. Patent Publication Number 2011/0256024, entitled "MODULAR ANALYTE MONITORING DEVICE", published Oct. 20, 2011;

U.S. Patent Publication Number 2010/0198142, entitled "MULTIFUNCTION ANALYTE TEST DEVICE AND METHODS THEREFORE", published Aug. 5, 2010;

U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011;

U.S. Pat. No. 5,294,404, entitled "REAGENT PACK FOR IMMUNOASSAYS" issued Mar. 15, 1994;

U.S. Pat. No. 5,063,081, entitled "METHOD OF MANUFACTURING A PLURALITY OF UNIFORM MICRO-FABRICATED SENSING DEVICES HAVING AN IMMOBILIZED LIGAND RECEPTOR" issued Nov. 5, 1991;

U.S. Pat. No. 7,419,821, entitled "APPARATUS AND METHODS FOR ANALYTE MEASUREMENT AND IMMUNOASSAY" issued Sep. 2, 2008;

U.S. Patent Publication Number 2004/0018577, entitled "MULTIPLE HYBRID IMMUNOASSAYS" published Jan. 29, 2004;

U.S. Pat. No. 7,682,833, entitled "IMMUNOASSAY DEVICE WITH IMPROVED SAMPLE CLOSURE" issued Mar. 23, 2010;

U.S. Pat. No. 7,723,099, entitled "IMMUNOASSAY DEVICE WITH IMMUNO-REFERENCE ELECTRODE" issued May 25, 2010; and Baj-Rossi et al. "FABRICATION AND PACKAGING OF A FULLY IMPLANTABLE BIOSENSOR ARRAY", (2013) IEEE, pages 166-169.

The terms "behavior related medical data" and "BRM data" shall mean information indicative of an action or conduct by a patient that will affect one or more physiologic characteristics of interest and/or information indicative of a present state experienced by a patient in connection with a physiologic characteristic of interest. As nonlimiting examples of information indicative of an act or conduct, BRM data may represent information related to a patient's diet (e.g., what, when and how much a patient ate or drank), information related to whether a patient is following a physician's instructions (e.g., exercising, walking, following a fluid regiment, taking medication at prescribed times), information related to nutritional supplements (e.g., what, when and how much a patient is taking as nutritional supplements), self-reported quality of life information from the patient, signs and symptoms indicating fatigue, lack of mobility/exercise and the like. The foregoing examples concern BRM data that is directly relate to actions and/or conduct by the patient. Optionally, the BRM data may indirectly relate to actions and/or conduct by the patient. For example, the BRM data may indicate how often and/or volumes of certain food products and liquids ordered by the patient through a home delivery service (e.g., how often and in what volume the patient orders certain groceries and other food products that may be delivered to a patient's home).

Further, as nonlimiting examples of information indicative of a present state, the BRM data may represent information indicating how a patient feels (e.g., headaches, shortness of breath, tired, chest pains). The BRM data may be manually entered by the patient or a third-party through various types of PDE devices. Optionally, the BRM data may be automatically entered by a PDE device based on electronic monitoring of actions and conduct by the patient, as well as other types of sensors.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The term "PA" shall mean pulmonary artery. The term "PAP" shall mean pulmonary arterial pressure.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "real-time" shall mean a time frame contemporaneous with normal or abnormal episode occurrences. For example, a real-time process or operation would occur during or immediately after (e.g., within minutes or seconds after) a cardiac event, a series of cardiac events, an arrhythmia episode, and the like. For example, the term "real-time" may refer to a time period substantially contemporaneous with an event of interest. The term "real-time," when used in connection with collecting and/or processing data utilizing an IMD, shall refer to processing operations performed substantially contemporaneous with a physiologic event of interest experienced by a patient. By way of example, in accordance with embodiments herein, cardiac activity signals are analyzed in real time (e.g., during a cardiac event or within a few minutes after the cardiac event). The term "real-time," when used in connection with a body generated analyte, shall refer to operations performed substantially contemporaneous with an occurrence of a characteristic of interest in a malnutrition state experienced by the patient. By way of example, in accordance with embodiments herein, the body generated analyte may correspond to serum albumin that is analyzed and utilized in a diagnosis and treatment recommendation. The analysis of the serum albumin and generation of the diagnosis and treatment recommendation are performed in real-time, namely while the patient is experiencing a certain malnutrition state, not to exceed 24 hours from the time the BGA was collected.

The term "on-demand" shall mean at any time that the system automatically determines that a measurement is warranted and without any need for patient action or intervention. As one example, an implantable sensor will collect pressure measurements "on-demand" automatically and in real-time in response to a data collection instruction from an IMD. As another example, an implantable sensor will collect pressure measurements "on-demand" automatically and in real-time in response to a data collection instruction from an external device such as a bedside monitor, smart phone, physician's programmer and the like. As another example, an implantable sensor will collect pressure measurements "on-demand" automatically and in real-time in response to a data collection schedule stored at the sensor, IMD or ED.

Embodiments may be implemented in connection with one or more implantable medical devices (IMDs). Nonlimiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

LIMD

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

S-IMD

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

ICM

Additionally or alternatively, the IMD may be a leadless cardiac monitor (ICM) that includes one or more structural and/or functional aspects of the device(s) described in U.S. Patent Application having Docket No. A15E1059, U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

The implantable medical sensor disclosed herein may implement one or more structural and/or functional aspects of the device(s) described in U.S. patent application Ser. No. 16/194,103, filed Nov. 16, 2018, and entitled "Wireless Sensor for Measuring Pressure;" U.S. patent application Ser. No. 14/733,450, filed Jun. 8, 2015, now U.S. Pat. No. 10,143,388, and entitled "Method of Manufacturing Implantable Wireless Sensor for In Vivo Pressure Measurement;" U.S. patent application Ser. No. 12/612,070, filed Nov. 4, 2009, and entitled "Method of Manufacturing Implantable Wireless Sensor for In Vivo Pressure Measurement," now U.S. Pat. No. 9,078,563; U.S. patent application Ser. No. 11/204,812, filed on Aug. 16, 2005 and entitled "Method of Manufacturing Implantable Wireless Sensor for In Vivo Pressure Measurement," now U.S. Pat. No. 7,621,036; U.S. patent application Ser. No. 11/157,375, filed Jun. 21, 2005 and entitled "Implantable Wireless Sensor for In Vivo Pressure Measurement," which are expressly incorporated herein by reference.

PIMD (Passive Implantable Medical Device)

Embodiments may be implemented in connection with one or more PIMDs. Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

All references, including publications, patent applications and patents, cited herein are hereby incorporated by reference to the same extent as if each reference were individually and specifically indicated to be incorporated by reference and were set forth in its entirety herein.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for collecting real-time on-demand measurements, the system comprising:
an implantable medical device (IMD) configured to be implanted in a patient, the IMD configured to sense and analyze a first type of patient data; and
an implantable sensor comprising:
a housing configured to be implanted in a blood vessel of a patient;
a power source;
a sensing circuit configured to sense a physiologic parameter of interest (PPOI) and to generate signals indicative of the PPOI;
a communications circuit configured to communicate with the IMD and an external device (ED);
a memory configured to store program instructions; and
one or more processors coupled to the memory, wherein the housing holds the power source, the sensing circuit, the communications circuit, the memory, and the one or more processors, wherein the program instructions are executable by the one or more processors to:

receive a data collection instruction from the IMD;

responsive to receiving the data collection instruction, collect real-time on-demand measurements for a second type of patient data by (i) activating the sensing circuit to generate the signals indicative of the PPOI; (ii) converting the signals to physiologic data indicative of the PPOI; and (iii) storing the physiologic data in the memory over a collection period, wherein the second type of patient data differs from the first type of patient data; and direct the communications circuit to transmit at least some of the physiologic data stored in the memory to at least one of the IMD or the ED at first times or intervals according to a predetermined data transmission schedule.

2. The system of claim 1, wherein the memory is configured to store a data collection schedule, and the one or more processors are further configured to collect the measurements based on the data collection schedule in real-time.

3. The system of claim 1, wherein the power source is configured to store an amount of energy to supply the sensing circuit, the communications circuit, and the one or more processors for at least a predetermined number of data collection operations and radiofrequency (RF) communication sessions, the data collection operations and RF communication sessions performed without any external energy delivery.

4. The system of claim 1, wherein the communications circuit further comprises a radiofrequency (RF) antenna configured to communicate with the IMD utilizing RF communications signals.

5. The system of claim 1, wherein the housing includes a first housing portion at a first end of the sensor, a second housing portion at a second end of the sensor opposite the first end, and a flexible cable disposed between and connected to the first and second housing portions, the sensor including a first electrode of the communications circuit held by the first housing portion and a second electrode of the communications circuit held by the second housing portion, the first electrode electrically coupled to the second electrode via the flexible cable, wherein the one or more processors are configured to direct the communications circuit to transmit the physiologic data by applying voltage bursts to the first and second electrodes to create a polarized electric field around the sensor.

6. The system of claim 1, wherein the one or more processors are configured to remain in a sleep mode until transitioning to a wake mode in response to receiving a wake-up instruction from a clock of the implantable sensor, the one or more processors configured to perform at least one of the activating, converting, storing, and directing operations when in the wake mode.

7. The system of claim 1 wherein the sensing circuit is configured to sense, as the PPOI, at least one of pressure, temperature, respiration, or a body generated analyte (BGA), wherein the signals generated by the sensing circuit represent electrical signals, for which at least one of voltage, current, capacitance, inductance or resistance varies based on a level of the PPOI.

8. The system of claim 1, wherein the power source includes a secondary battery, the secondary battery electrically connected to one of (i) the IMD via a direct wired connection to receive electrical power from the IMD or (ii) an energy harvesting unit of the sensor, the energy harvesting unit comprising a coil configured to inductively connect to an external recharge device to transfer electrical power from the external recharge device to the secondary battery via the energy harvesting unit.

9. The system of claim 1, wherein the one or more processors are configured to collect the measurements at second times or intervals according to a predetermined data collection schedule, stored in the memory of the sensor, to store the physiologic data in the memory over the collection period, and wherein the second times or intervals of the data collection schedule are more frequent than the first times or intervals of the data transmission schedule.

10. The system of claim 1, wherein the housing of the implantable sensor includes one or more loop wires that extend from the housing for anchoring the implantable sensor to the blood vessel of the patient.

11. The system of claim 1, wherein the implantable sensor is a pressure sensor and the PPOI is blood pressure; and wherein the IMD includes sensing circuitry coupled to electrodes and configured to sense electrical cardiac activity data, a processor that, when executing program instructions, is configured to analyze the cardiac activity data.

12. The system of claim 1, wherein the processor of the IMD is configured to analyze the physiologic data and based thereon change a therapy delivered by the IMD.

13. The system of claim 1, wherein the communications circuit is configured to wirelessly communicate with the IMD and the ED utilizing at least one of radio frequency wireless communication or conductive communication.

14. The system of claim 1, wherein the processor of the IMD is configured to determine whether the physiologic data indicates a change that prompts a modification of treatment provided by the IMD.

15. The system of claim 14, wherein the processor is further configured to modify at least one parameter of the therapy provided by the IMD based on the determination.

16. A method comprising:

sensing and analyzing a first type of patient data utilizing an implantable medical device (IMD) implanted in a patient; and receiving, via a communications circuit of an implantable sensor implanted within the patient, a data collection instruction communicated by the IMD, wherein the implantable sensor includes a housing configured to be implanted in a blood vessel of the patient;

collecting real-time on-demand measurements for a second type of patient data via the implantable sensor in response to receiving the data collection instruction, wherein the collecting operation comprises (i) activating a sensing circuit of the implantable sensor to sense a physiologic parameter of interest (PPOI) and generate signals indicative of the PPOI, the sensing circuit powered by a power source onboard the implantable sensor; (ii) converting the signals to physiologic data indicative of the PPOI via one or more processors of the implantable sensor; and (iii) storing the physiologic data in a memory of the implantable sensor, wherein the second type of patient data differs from the first type of patient data, wherein the housing holds the power source, the sensing circuit, the communications circuit, the memory, and the one or more processors; and directing the communications circuit of the implantable sensor to transmit at least some of the physiologic data stored in the memory to at least one of the IMD or an external device (ED) outside of the patient in response to receiving the data collection instruction.

17. The method of claim 16, further comprising collecting the real-time on-demand measurements via the implantable sensor at first times or intervals according to a predetermined data collection schedule stored in the memory in addition to collecting the real-time on-demand measurements in response to receiving the data collection instruction.

18. The method of claim 17, further comprising directing the communications circuit to transmit radiofrequency (RF) communications signals comprising the physiologic data stored in the memory to the at least one of the IMD or the ED at second times or intervals according to a predetermined data transmission schedule, in addition to directing the communications circuit to transmit the at least some of the physiologic data to the at least one of the IMD or the ED on-demand in response to receiving the data collection instruction.

19. The method of claim 18, wherein the first times or intervals of the data collection schedule are more frequent than the second times or intervals of the data transmission schedule.

20. The method of claim 16, further comprising assembling the implantable sensor to include, as the housing, a first housing portion, a second housing portion, and a flexible cable disposed between and connected to the first and second housing portions, the assembling operation comprising:

installing a first electrode of the communications circuit to the first housing portion;

installing a second electrode of the communications circuit to the second housing portion; and electrically coupling the first electrode to the second electrode via the flexible cable, wherein the directing operation to direct the communications circuit of the sensor to transmit the physiologic data comprises applying voltage bursts to the first and second electrodes to create a polarized electric field around the sensor.

21. The method of claim 16, further comprising directing the communications circuit to transmit radiofrequency (RF) communications signals comprising at least some of the physiologic data stored in the memory to the IMD in response to receiving the data collection instruction.

22. The method of claim 16, further comprising analyzing the physiologic data and changing a therapy delivered by the IMD based on the analysis.

23. A system for collecting real-time on-demand measurements, the system comprising:

an implantable medical device (IMD) configured to be implanted in a patient, the IMD configured to sense and analyze a first type of patient data; and an implantable sensor comprising:

a housing configured to be implanted in a blood vessel of a patient;

a power source;

a sensing circuit configured to sense a physiologic parameter of interest (PPOI) and to generate signals indicative of the PPOI;

a communications circuit configured to communicate with an implantable medical device (IMD) implanted within the patient and an external device (ED);

a memory configured to store program instructions and to store a data collection schedule; and one or more processors coupled to the memory, wherein the housing holds the power source, the sensing circuit, the communications circuit, the memory, and the one or more processors, wherein the program instructions are executable by the one or more processors to:

collect real-time on-demand measurements for a second type of patient data, based on the data collection schedule, by (i) activating the sensing circuit to generate the signals indicative of the PPOI; (ii) converting the signals to physiologic data indicative of the PPOI; and (iii) storing the physiologic data in the memory over a collection period, wherein the second type of patient data differs from the first type of patient data; and direct the communications circuit to transmit the physiologic data stored in the memory to the IMD at intervals.

24. The system of claim 23, wherein the implantable sensor is a pressure sensor and the PPOI is blood pressure; and wherein the IMD includes sensing circuitry coupled to electrodes and configured to sense electrical cardiac activity data, a processor that, when executing program instructions, is configured to analyze the cardiac activity data.

25. The system of claim 23, wherein the processor of the IMD is configured to analyze the physiologic data and based thereon change a therapy delivered by the IMD.

* * * * *